United States Patent
Rise et al.

(10) Patent No.: US 10,688,303 B2
(45) Date of Patent: Jun. 23, 2020

(54) THERAPY TARGET SELECTION FOR PSYCHIATRIC DISORDER THERAPY

(75) Inventors: Mark T. Rise, Monticello, MN (US); Jonathon E. Giftakis, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 2304 days.

(21) Appl. No.: 12/425,758

(22) Filed: Apr. 17, 2009

(65) Prior Publication Data

US 2009/0264954 A1 Oct. 22, 2009

Related U.S. Application Data

(60) Provisional application No. 61/046,236, filed on Apr. 18, 2008.

(51) Int. Cl.
*A61N 1/36* (2006.01)

(52) U.S. Cl.
CPC ............................. *A61N 1/36082* (2013.01)

(58) Field of Classification Search
CPC ...... A61N 1/36025; A61N 2001/36039; A61N 2001/36082; A61N 2001/36096; A61N 2001/36135; A61N 2001/36139
USPC .......................... 607/45, 59, 62, 139; 600/544
See application file for complete search history.

(56) References Cited

U.S. PATENT DOCUMENTS

| | | | |
|---|---|---|---|
| 5,299,569 A | 4/1994 | Wernicke et al. | |
| 6,128,537 A | 10/2000 | Rise | |
| 6,176,242 B1 | 1/2001 | Rise | |
| 6,263,237 B1 | 7/2001 | Rise | |
| 6,418,344 B1 | 7/2002 | Rezai et al. | |
| 6,609,030 B1 | 8/2003 | Rezai et al. | |
| 6,622,047 B2 | 9/2003 | Barrett et al. | |
| 6,708,064 B2 | 3/2004 | Rezai | |
| 6,782,292 B2 * | 8/2004 | Whitehurst | 607/45 |
| 7,313,442 B2 * | 12/2007 | Velasco et al. | 607/45 |
| 7,346,395 B2 | 3/2008 | Lozano et al. | |
| 7,353,065 B2 | 4/2008 | Morrell | |
| 2005/0027284 A1 | 2/2005 | Lozano et al. | |

(Continued)

FOREIGN PATENT DOCUMENTS

| | | |
|---|---|---|
| WO | WO 2004/052183 A2 | 6/2004 |
| WO | WO 2006/053143 A2 | 5/2006 |

OTHER PUBLICATIONS

Hamilton, Max. "A Rating Scale for Depression." J. Neurol. Neurosurg. Psychiat., 1960.*

(Continued)

*Primary Examiner* — Eugene T Wu
(74) *Attorney, Agent, or Firm* — Shumaker & Sieffert, P.A.

(57) ABSTRACT

Target tissue sites for therapy delivery to a patient may be selected based on the patient symptoms or a patient mood state. The therapy delivery may be used to manage a psychiatric disorder of the patient. Selected therapy sites may be weighted based on factors, such as the severity of the patient symptom or mood state or the type of patient symptom or mood state. In some cases, therapy delivery to the patient may be controlled based on the weighting factors. For example, the weighting factors may control the intensity of the therapy delivery or the frequency of the therapy delivery. In some examples, the weighting factors may dynamically change based on the patient's changing symptoms or mood disorders.

44 Claims, 9 Drawing Sheets

(56) References Cited

U.S. PATENT DOCUMENTS

| | | | |
|---|---|---|---|
| 2006/0058856 A1* | 3/2006 | Morrell | 607/46 |
| 2006/0136008 A1* | 6/2006 | Tadlock | 607/45 |
| 2006/0259099 A1 | 11/2006 | Goetz et al. | |
| 2007/0027499 A1 | 2/2007 | Maschino et al. | |
| 2007/0055320 A1 | 3/2007 | Weinand | |
| 2007/0088404 A1 | 4/2007 | Wyler et al. | |
| 2007/0173901 A1 | 7/2007 | Reeve | |
| 2007/0179558 A1 | 8/2007 | Gliner et al. | |
| 2007/0203540 A1 | 8/2007 | Goetz et al. | |
| 2007/0265489 A1 | 11/2007 | Fowler et al. | |

OTHER PUBLICATIONS

Notification of Transmittal of the International Search Report and the Written Opinion of the International Searching Authority or the Declaration dated Nov. 19, 2009 for corresponding PCT Application No. PCT/US2009/040957 (12 pgs.).

Schlaepfer et al., "Deep Brain Stimulation to Reward Circuitry Alleviates Anhedonia in Refractory Major Depression," Neuropsychopharmacology, Feb. 2007 (10 pgs.).

Mayberg, "Modulating dysfunctional limbic-cortical circuits in depression: towards development of brain-based algorithms for diagnosis and optimized treatment," British Medical Bulletin, 65, pp. 193-207 (2003).

"Brain Pacemaker," http://en.wikipedia.org/wiki/Brain_pacemaker, printed Jun. 3, 2009 (2 pgs.).

"Neurobiology of Depresseion," http://www.gatewaypsychiatric.com/Patient%20Resourses/Mood%20Disorders%20Info/Neurobiology%20of%20Depression.htm, printed Jun. 3, 2009 (3 pgs.).

"DBS: An Overview," http://biomed.brown.edu/Courses/BI108/BI108_2007_Groups/group02/dbsoverview.html, printed.Jun. 3, 2009 (4 pgs.).

U.S. Appl. No. 61/046,236, filed Apr. 18, 2008, entitled: "Therapy Target Selection for Psychiatric Disorder Therapy,".

Notification Concerning Transmittal of International Preliminary Report on Patentability, dated Oct. 28, 2010 for corresponding PCT/U82009/040957, 7 pgs.

* cited by examiner

| SYMPTOM | TARGET TISSUE SITE |
|---|---|
| FATIGUE | VENTRAL STRIATUM (VC/VS) |
| ANHEDONIA | VENTRAL STRIATUM (VC/VS) |
| DEPRESSED MOOD | CINGULATE CORTEX (CG25) |
| DEPRESSED MOOD | BRODMANN AREA 10 |
| LOSS OF ENERGY | VENTRAL STRIATUM (VC/VS) |
| ANXIETY | BRODMANN AREA 11 |

| PATIENT MOOD STATE | TARGET TISSUE SITE |
|---|---|
| DEPRESSIVE MOOD | VENTRAL STRIATUM (VC/VS) |
| MANIC MOOD | NUCLEUS ACCUMBENS |

THERAPY TARGET SELECTION FOR PSYCHIATRIC DISORDER THERAPY

This application claims the benefit of U.S. Provisional Application No. 61/046,236 to Rise et al., entitled, "THERAPY TARGET SELECTION FOR PSYCHIATRIC DISORDER THERAPY" and filed on Apr. 18, 2008, the entire content of which is incorporated herein by reference.

TECHNICAL FIELD

The disclosure relates to therapy delivery, and, more particularly, therapy delivery to manage psychiatric disorders.

BACKGROUND

Implantable medical devices, such as electrical stimulators or therapeutic agent delivery devices, may be used in different therapeutic applications, such as deep brain stimulation (DBS) or delivery of pharmaceutical agent, insulin, pain relieving agent or anti-inflammatory agent to a target tissue site within a patient. DBS may be useful for managing a variety of patient conditions, such as movement disorders, seizure disorders (e.g., epilepsy) or mood disorders. In some DBS systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within the brain of the patient with the aid of one or more fluid delivery elements, such as a catheter.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, and an amplitude, which may be a current or voltage amplitude, a pulse width, and a pulse rate for the pulses. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

SUMMARY

In general, the disclosure is directed to selecting target tissue sites within a brain of a patient for delivering therapy to manage a psychiatric disorder and delivering therapy to the selected target tissue sites. The target tissue sites may be selected based on the patient's symptoms or patient mood state. For example, a particular target tissue site may be more useful for managing one or more patient symptoms or one or more mood states than other target tissue sites. In examples in which the psychiatric disorder therapy includes electrical stimulation, in some examples, therapy may be delivered to the two or more target tissue sites by selecting different combinations of electrodes that are available for stimulation. Based on the implant location of the electrodes, different combinations of electrodes may map to different target tissue sites.

In some cases, weighting factors are established for the selected target tissue sites. The weighting factors may be based on the severity of the patient symptoms or mood states, and/or the type of patient symptoms or mood states observed for the patient. The weighting factors may be used to control therapy delivery to the patient. For example, the weighting factors may control the intensity of stimulation provided to a particular target tissue site or the frequency of the stimulation provided to the target tissue sites. In addition, in some examples described herein, different therapy programs may be associated with different weighting factors, and therapy may be delivered to a target tissue site according to the therapy program associated with the weighting factor for the target tissue site. In the case of electrical stimulation, a therapy program may include an electrode combination (e.g., selected electrodes and respective polarities), an amplitude, which may be a current or voltage amplitude, a signal duration (e.g., a pulse width in the case of stimulation pulses), and a frequency (e.g., a pulse rate in the case of stimulation pulses). In some embodiments, the weights given to the target tissue sites are dynamic, and may be changed as the patient's symptoms change.

As described herein, a therapy system may be configured to deliver therapy to two or more target tissue sites within the patient. The therapy sites may be selected based on detected patient symptoms or mood states. If more than two symptoms or mood states are detected, therapy may be delivered to the two or more target tissue sites associated with the patient symptoms substantially simultaneously, or on an interleaved or alternating basis.

In one aspect, the disclosure is directed to a method comprising determining a first patient symptom and a second patient symptom of a patient, wherein the first and second patient symptoms differ, selecting a first target tissue site for psychiatric disorder therapy delivery based on the first patient symptom, and selecting a second target tissue site for the psychiatric disorder therapy delivery based on the second patient symptom, wherein the second target tissue site is different than the first target tissue site.

In another aspect, the disclosure is directed to a method comprising selecting a first target tissue site for psychiatric disorder therapy delivery, selecting a second target tissue site for the psychiatric disorder therapy delivery, establishing weighting factors to the first and second target tissue sites, and delivering the psychiatric disorder therapy delivery to the first and second target tissue sites according to the weighting factors.

In another aspect, the disclosure is directed to a method comprising detecting a patient mood state, wherein the patient mood state is characterized by at least a first patient symptom and a second patient symptom that is different than the first patient symptom, delivering therapy to a first target tissue site that is associated with the first patient symptom, and delivering therapy to a second target tissue site that is associated with the second patient symptom.

In another aspect, the disclosure is directed to a method comprising detecting a first patient symptom, detecting a second patient symptom, delivering therapy to a first target tissue site that is associated with the first patient symptom in response to detecting the first patient symptom, and delivering therapy to a second target tissue site that is associated with the second patient symptom in response to detecting the second patient symptom.

In another aspect, the disclosure is directed to a system comprising a memory that stores first information associating patient symptoms with target tissue sites for delivery of psychiatric disorder therapy, and a processor that determines a first patient symptom and a second patient symptom of a patient, wherein the first and second patient symptoms differ, selects a first target tissue site for psychiatric disorder therapy delivery based on the first patient symptom and the first information, and selects a second target tissue site for the psychiatric disorder therapy delivery based on the second patient symptom and the first information, wherein the second target tissue site is different than the first target tissue site.

In another aspect, the disclosure is directed to a system comprising a processor that receives information indicating a first patient symptom and a second patient symptom of a patient, wherein the first and second patient symptoms differ, selects a first target tissue site for psychiatric disorder therapy delivery based on the first patient symptom, and selects a second target tissue site for the psychiatric disorder therapy delivery based on the second patient symptom, wherein the second target tissue site is different than the first target tissue site. The system further comprises a medical device that delivers therapy to the first and second target tissue sites.

In another aspect, the disclosure is directed to a system comprising a medical device, and a processor that detects a patient mood state, where the patient mood state is characterized by at least a first patient symptom and a second patient symptom that is different than the first patient symptom, and controls the medical device to deliver therapy to a first target tissue site that is associated with the first patient symptom and a second target tissue site that is associated with the second patient symptom.

In another aspect, the disclosure is directed to a method comprising determining first and second mood states for a psychiatric disorder of a patient, wherein the first and second mood states differ, selecting a first target tissue site for psychiatric disorder therapy delivery based on the first mood state, and select a second target tissue site for the psychiatric disorder therapy delivery based on the second mood state, wherein the second target tissue site is different than the first target tissue site.

In another aspect, the disclosure is directed to a method comprising detecting a first patient mood state of a patient, detecting a second patient mood state of the patient, delivering psychiatric disorder therapy to a first target tissue site within the patient in response to detecting the first patient mood state, and delivering psychiatric disorder therapy to the patient to a second target tissue site in response to detecting the second patient mood state.

In another aspect, the disclosure is directed to a system comprising means for determining first and second mood states for a psychiatric disorder of a patient, wherein the first and second mood states differ, means for selecting a first target tissue site for psychiatric disorder therapy delivery based on the first mood state, and means for selecting a second target tissue site for the psychiatric disorder therapy delivery based on the second mood state, wherein the second target tissue site is different than the first target tissue site.

In another aspect, the disclosure is directed to a system comprising means for detecting a first patient mood state of a patient, means for detecting a second patient mood state of the patient, means for delivering psychiatric disorder therapy to a first target tissue site within the patient in response to detecting the first patient mood state, and means for delivering psychiatric disorder therapy to the patient to a second target tissue site in response to detecting the second patient mood state.

In another aspect, the disclosure is directed to a system comprising a memory that stores information associating patient mood states with target tissue sites for delivery of psychiatric disorder therapy, and a processor that determines first and second mood states for a psychiatric disorder of a patient, selects a first target tissue site for the psychiatric disorder therapy delivery based on the first mood state and the information, and selects a second target tissue site for the psychiatric disorder therapy delivery based on the second mood state and the first information, wherein the second target tissue site is different than the first target tissue site.

In another aspect, the disclosure is directed to a system comprising a processor that receives information indicating a first patient mood state and a second patient mood state of a patient, wherein the first and second patient mood state differ, selects a first target tissue site for psychiatric disorder therapy delivery based on the first patient mood state, and selects a second target tissue site for the psychiatric disorder therapy delivery based on the second patient mood state, wherein the second target tissue site is different than the first target tissue site, and a medical device that delivers therapy to the first and second target tissue sites.

In another aspect, the disclosure is directed to a system comprising a medical device, and a processor that detects a first patient mood state and a second patient mood state, wherein the first and second patient mood state differ, and controls the medical device to deliver therapy to a first target tissue site that is associated with the first patient mood state and a second target tissue site that is associated with the second patient mood state.

In another aspect, the disclosure is directed to a system comprising means for determining a first patient symptom and a second patient symptom of a patient, wherein the first and second patient symptoms differ, means for selecting a first target tissue site for psychiatric disorder therapy delivery based on the first patient symptom, and means for selecting a second target tissue site for the psychiatric disorder therapy delivery based on the second patient symptom, wherein the second target tissue site is different than the first target tissue site.

In another aspect, the disclosure is directed to a system comprising means for selecting a first target tissue site for psychiatric disorder therapy delivery, means for selecting a second target tissue site for the psychiatric disorder therapy delivery, means for establishing weighting factors for the first and second target tissue sites, and means for delivering the psychiatric disorder therapy delivery to the first and second target tissue sites according to the weighting factors.

In another aspect, the disclosure is directed to a system comprising means for detecting a patient mood state, wherein the patient mood state is characterized by at least a first patient symptom and a second patient symptom that is different than the second patient symptom, means for delivering therapy to a first target tissue site that is associated with the first patient symptom, and means for delivering therapy to a second target tissue site that is associated with the second patient symptom.

In another aspect, the disclosure is directed to a system comprising means for detecting a first patient symptom, means for detecting a second patient symptom, means for delivering therapy to a first target tissue site that is associated with the first patient symptom in response to detecting the first patient symptom, and means for delivering therapy to a second target tissue site that is associated with the second patient symptom in response to detecting the second patient symptom.

In another aspect, the disclosure is directed to a computer-readable medium containing instructions. The instructions cause a programmable processor to perform any of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages of the invention will be apparent from the description and drawings, and from the claims.

DETAILED DESCRIPTION

Figure 1:
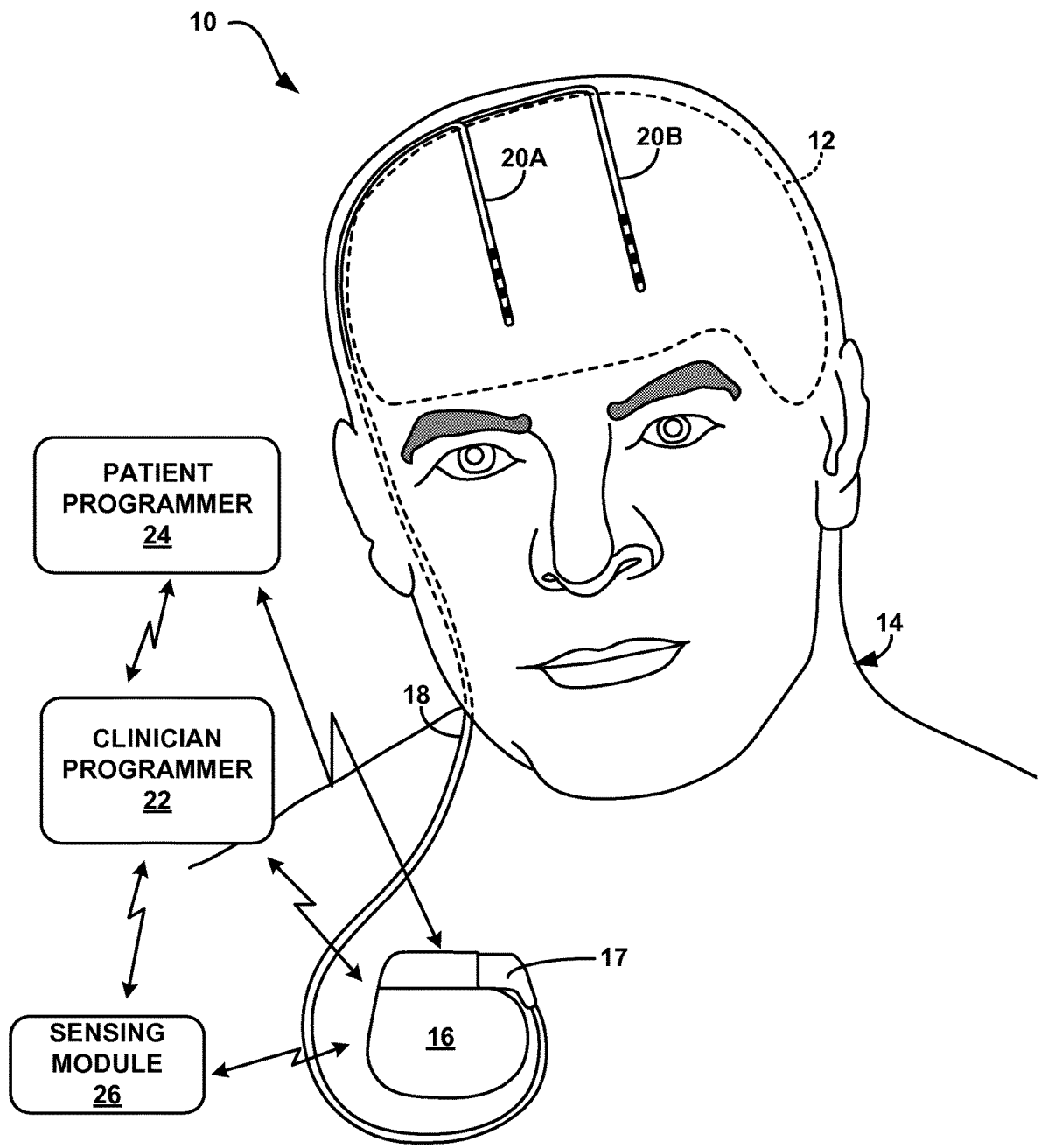
FIG. 1 is a conceptual diagram illustrating an example therapy system including an implantable medical device, a patient programmer, and a clinician programmer.

FIG. 1 is a conceptual diagram illustrating an embodiment of a therapy system 10 that delivers therapy to brain 12 of patient 14 in order to help manage a patient condition, such as a psychiatric disorder. Examples of psychiatric disorders that therapy system 10 may be useful for managing include major depressive disorder (MDD), bipolar disorder, anxiety disorders, post traumatic stress disorder, dysthymic disorder, and obsessive-compulsive disorder (OCD). In some cases, patient 14 may suffer from symptoms of more than one psychiatric disorder, such as MDD and anxiety. While patient 14 is generally referred to as a human patient, other mammalian or non-mammalian patients are also contemplated. Therapy system 10 includes implantable medical device (IMD) 16, connector block 17, lead extension 18, leads 20A and 20B, clinician programmer 22, patient programmer 24, and sensing module 26.

In the embodiment shown in FIG. 1, therapy system 10 may be referred to a deep brain stimulation (DBS) system because IMD 16 provides electrical stimulation therapy to one or more tissue sites within brain 12, e.g., under the dura mater of brain 12. In other embodiments, leads 20 may be positioned to deliver therapy to a surface of brain 12 (e.g., the cortical surface of brain 12) in addition to or instead of tissue within brain 12. In particular, as shown in FIG. 1, IMD 16 may include a therapy module that delivers electrical stimulation therapy to two or more different target tissue sites within brain 12 via leads 20A and 20B. In other examples of therapy system 10, IMD 16 can deliver a therapeutic agent (e.g., a drug) to two or more target tissue sites within brain 12 to manage a psychiatric disorder of patient 14. In addition, in other examples, IMD 16 can deliver electrical stimulation to a first target tissue site within brain 12 and a therapeutic agent to a second target tissue site within brain 12 that is different than the first target tissue site to manage a psychiatric disorder of patient 14. The techniques for selecting the target tissue sites and delivering therepy thereto are applicable to any therapy system that delivers therapy to at least two different tissue sites within brain 12, regardless of the types of therapy.

As discussed in further detail below, the delivery of electrical stimulation to the two or more different target tissue sites may be based on respective weighting factors for the target tissue sites. Weighting factors may be, for example, weighting variables or weighting coefficients that control therapy. For example, based on the weighting factors, IMD 16 may deliver different intensities of stimulation to the two or more target tissue sites, such as by delivering stimulation at different frequencies, different pulse widths, different stimulation burst patterns, different durations, and the like, to the two or more different target tissue sites. In some examples, weighting may determine a percentage of intensity as a percentage of a maximum intensity, which may be specific to the target tissue site.

Therapy delivery to the two or more different target tissue sites may be based on detected patient mood states or patient symptoms. A symptom may be, for example, a manifestation of a psychiatric disorder for which therapy system 10 provides therapy to manage. Patient symptoms may be indicative of a common mood state of patient 14 or different mood states. A symptom may be subjectively observed by patient 14 and/or may be an objective indication of the psychiatric condition. A mood state may be an affective state of patient 14, which may be related to a psychiatric disorder. A mood state may be characterized by one or more symptoms. In addition or alternatively, a particular patient mood may be a symptom of a psychiatric disorder.

Each therapy site may be associated with a single patient symptom or mood state, or more than one patient or mood state. In addition, a single symptom may be addressed by therapy delivery to more than one target tissue site within patient 14. Example techniques for selecting the two or more target tissue sites are described in further detail below, e.g., with reference to FIGS. 5-10. Either the symptom or a mood state may indicate the occurrence of a psychiatric episode. In addition, the occurrence of a symptom may be indicative of the occurrence of a particular mood state. The occurrence of one or more psychiatric episodes may indicate that the patient has a psychiatric disorder. Accordingly, symptoms or mood states of psychiatric disorders may include one or more symptoms of psychiatric episodes that result from the disorder. However, one or more symptoms of a psychiatric disorder may occur without the occurrence of a psychiatric episode, which is typically characterized by a particular number of symptoms occurring within the same time period (e.g., a few days to a week or more).

In some embodiments, in addition to selecting target therapy sites within brain 12 that are specific to the patient symptoms or mood states, IMD 16 may deliver substantially continuous stimulation (e.g., on a particular schedule setting on and off cycles) to one or more target tissue sites within brain 12. For example, leads 20 may be positioned to deliver substantially continuous stimulation to a ventral striatum (also referred to as a VC/VS) or the cingulate cortex (e.g., the Brodmann area 25 (CGX25)) of brain 12, regardless of the specific patient symptoms or mood states that are detected or diagnosed for patient 14.

Although electrical stimulation is primarily referred to throughout the description of FIGS. 1-10, in other embodiments, IMD 16 may be configured to deliver one or more therapeutic agents to patient 14 instead of, or in addition to, electrical stimulation. The one or more therapeutic agents may be delivered to two or more target tissue sites within brain 12, and the target tissue sites may be selected, and, in some cases, weighted, according to the techniques described herein. In this case, the weighting factors established for each therapy site may be used to determine relative or absolute therapy dosage amounts (e.g., intensity of stimulation or the dosage of a therapeutic agent), dosage rates (e.g., frequency of therapy delivery, electrical stimulation burst patterns), and the like.

As shown in FIG. 1, IMD 16 may be implanted within a chest cavity of patient 14. In other embodiments, IMD 16 may be implanted within other regions of patient 14, such as a subcutaneous pocket in the abdomen of patient 14 or proximate the cranium of patient 14. Implanted lead extension 18 is coupled to IMD 16 via connector block 17, which may include, for example, electrical contacts that electrically couple to respective electrical contacts on lead extension 18. The electrical contacts electrically couple the electrodes carried by leads 20A and 20B (collectively "leads 20") to IMD 16. Lead extension 18 traverses from the implant site of IMD 16 within a chest cavity of patient 14, along the neck of patient 14 and through the cranium of patient 14 to access brain 12.

In the example shown in FIG. 1, leads 20 are implanted within the right and left hemispheres, respectively, of brain 12 in order to deliver electrical stimulation to two or more therapy delivery sites within brain 12. The two or more therapy delivery sites may be selected based on many factors, such as the type of patient condition for which therapy system 10 is implemented to manage or the patient symptoms characterizing the patient condition. For example, while two patients may be diagnosed with a particular mood disorder, the two patients may exhibit different symptoms, and leads 20 may be implanted to deliver stimulation to different regions of the patients' brains. Different neurological or psychiatric disorders may be associated with activity in one or more of regions of brain 12, which may differ between patients.

For example in the case of MDD, bipolar disorder, OCD, or other anxiety disorders, leads 20 may be implanted to deliver electrical stimulation to the anterior limb of the internal capsule of brain 12, and only the ventral portion of the anterior limb of the internal capsule (also referred to as a VC/VS), the subgenual component of the cingulate cortex, anterior cingulate cortex Brodmann area 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, or any combination thereof.

As described in further detail below, the location of leads 20 within or on a surface of brain 12 may be selected to deliver therapy to two or more regions of brain 12, which may be two or more separate brain structures or may include two sites within a common structure. The target therapy delivery sites may be selected based on patient symptoms. It is believed that therapy delivery to a particular region of brain 12 may provide more effective therapy for mitigating a patient symptom compared to other regions of brain 12. Accordingly, in order to mitigate the patient symptom, leads 20 may be positioned to deliver therapy to the identified brain region. Further, if patient 14 exhibits multiple symptoms, leads 20 may be positioned to deliver therapy to respective regions of brain 12 identified to be associated with each of the patient symptoms.

As an example of a relationship between patient symptoms and one or more target tissue sites within brain 12, anhedonia may be associated with at least one of the nucleus accumbens, which forms part of the ventral striatum, the ventral tegmental area (VTA), medial forebrain bundle (MFB), the prefrontal cortex, septum in brain 12 (also referred to as septal nuclei), or one or more amygdala. The MFB carries neural information between the nucleus accumbens and VTA. Accordingly, therapy delivery to one of the aforementioned sites of brain 12 may help manage a patient symptom of anhedonia, which may refer to a lack of pleasure or a lack of the capacity to experience it. Anhedonia may be a symptom of MDD.

As another example, a diminished ability to think or concentrate, which may be a clinical symptom of MDD, may be associated with at least one of the anterior cingulate gyrus. Another patient symptom of a psychiatric disorder may include indecisiveness. For example, indecisiveness may be a symptom of MDD. A symptom of indecisiveness may be associated with the orbitofrontal cortex (OFC), which is involved in decision making cognitive processes. Therapy delivery to the OFC may help reduce or eliminate the patient's indecisiveness.

Another patient symptom of a psychiatric disorder may include fatigue and/or loss of energy. Fatigue and/or loss of energy may be associated with MDD. The ascending reticular activating system may be associated with a patient symptom of fatigue and/or loss of energy. Accordingly, delivery of stimulation to the ascending reticular activating system may help mitigate feelings of fatigue and/or loss of energy.

Another patient symptom of a psychiatric disorder may include depressed mood. A depressed mood may be a symptom of MDD or bipolar disorder. Therapy delivery to the internal capsule and/or VC/VS may help manage a depressed mood symptom. Therapy delivery to the internal capsule and/or VC/VS may also help a patient symptom characterized by recurrent thoughts of death or suicide ideation. Accordingly, the VC/VS may be associated with both patient symptoms of depressed mood and recurrent thoughts of death or suicide ideation.

Each of the patient symptoms may be indicative of a particular patient mood state. For example, a depressed mood or fatigue may be indicative of a severely depressed mood state. Thus, detection of one or more symptoms may also be used to determine a patient mood state.

Although leads 20 are shown in FIG. 1 as being coupled to a common lead extension 18, in other embodiments, leads 20 may be coupled to IMD 16 via separate lead extensions or directly coupled to IMD 16. Leads 20 may deliver electrical stimulation to treat any number of neurological disorders or diseases in addition to psychiatric disorders, such as movement disorders or seizure disorders. Examples of movement disorders include a reduction in muscle control, motion impairment or other movement problems, such as rigidity, bradykinesia, rhythmic hyperkinesia, nonrhythmic hyperkinesia, tremor, and akinesia.

Leads 20 may be implanted within a desired location of brain 12 via any suitable technique, such as through respective burr holes in a skull of patient 14 or through a common burr hole in the cranium. Leads 20 may be placed at any location within brain 12 such that the electrodes of the leads are capable of providing electrical stimulation to targeted tissue during treatment. Electrical stimulation generated from the signal generator (not shown) within the therapy module of IMD 16 may help prevent the onset of events associated with the patient's psychiatric disorder or mitigate symptoms of the psychiatric disorder.

For example, electrical stimulation therapy delivered by IMD 16 to a first target tissue site (e.g., nucleus accumbens) within brain 12 may help prevent a manic event if patient 14 has a bipolar disorder while electrical stimulation therapy delivered by IMD 16 to a second target tissue site (e.g., VC/VS or CG25) within brain 12 may help prevent a depressive disorder. The exact therapy parameter values of the stimulation therapy, such as the amplitude or magnitude of the stimulation signals, the duration of each signal, the waveform of the stimuli (e.g., rectangular, sinusoidal or ramped signals), the frequency of the signals, and the like, may be specific for the particular target stimulation site (e.g., the region of the brain) involved as well as the particular patient and patient condition.

In the case of stimulation pulses, the stimulation therapy may be characterized by selected pulse parameters, such as pulse amplitude, pulse rate, and pulse width. The stimulation therapy may be cycled on and off with duty cycle, which may be a programmable value. Stimulation therapy may also be automatically programmed to occur only for specific periods of time during specific times of the day, e.g., according to a stored therapy schedule. In addition, if different electrodes are available for delivery of stimulation, the therapy may be further characterized by different electrode combinations, which may define the selected electrodes and their respective polarities. Known techniques for determining the optimal stimulation parameters may be employed. In one embodiment, electrodes of leads 20 are positioned to deliver stimulation therapy to an anterior limb of the internal capsule of brain 12 in order to manage symptoms of a MDD of patient 14, and stimulation therapy is delivered via a select combination of the electrodes to the anterior capsule with electrical stimulation including a frequency of about 2 hertz (Hz) to about 2000 Hz, a voltage amplitude of about 0.5 volts (V) to about 20 V, and a pulse width of about 60 microseconds (µs) to about 4 milliseconds (ms). However, other embodiments may implement stimulation therapy including other stimulation parameters.

The electrodes of leads 20 are shown as ring electrodes in FIG. 1. Ring electrodes may be relatively easy to program and are typically capable of delivering an electrical field to any tissue adjacent to leads 20. In other embodiments, the electrodes of leads 20 may have different configurations. For example, the electrodes of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. The multiple electrodes may be positioned to define different "levels" that are spaced generally along a longitudinal axis of the respective lead 20A or 20B. In this manner, electrical stimulation may be directed to a specific direction from leads 20 to enhance therapy efficacy and reduce possible adverse side effects from stimulating a large volume of tissue. In some embodiments, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 14.

In some embodiments, leads 20 may include sensing electrodes positioned to detect electrical signals (also referred to as bioelectrical signals or brain signals) within one or more region of patient's brain 12. Alternatively, another set of sensing electrodes may monitor the electrical signal, which may be coupled to leads 20 or a separate lead that is coupled to IMD 16. The monitored electrical signals may include an electroencephalogram (EEG) signal. Electrodes implanted closer to the target region of brain 12 may help generate an EEG signal that provides more useful information than an EEG generated via a surface electrode array because of the proximity to brain 12. The EEG signal that is generated from implanted electrode array may also be referred to as an electrocorticography (ECoG). In some embodiments, the electrical signals from within brain 12 may be used to detect a patient mood state, as described below with reference to FIG. 7. In other embodiments, an EEG signal of patient 14 may be monitored with external electrodes, e.g., scalp electrodes.

Sensing module 26 is configured to monitor a physiological signal of patient 14, which may be used to determine a patient mood state, as described in commonly-assigned U.S. Pat. No. 9,333,350 to Rise et al., which is entitled, "PSYCHIATRIC DISORDER THERAPY CONTROL," which was filed on the same date as the present disclosure and issued on May 10, 2016, and U.S. Provisional Application No. 61/046,210 to Rise et al., entitled, "PSYCHIATRIC DISORDER THERAPY CONTROL" and filed on Apr. 18, 2008. U.S. Provisional Application No. 61/046,210 to Rise et al. and U.S. Pat. No. 9,333,350 to Rise et al. are incorporated herein by reference in their entireties.

As described in U.S. Pat. No. 9,333,350 to Rise et al. and U.S. Provisional Application No. 61/046,210 to Rise et al., a signal indicative of the physiological parameter (i.e., a physiological signal) of patient 14 may be monitored before and after the delivery of therapy according to a particular therapy program. In response to the delivery of therapy, the physiological signal may change. Thus, the change in the signal during a post-stimulation period (after the delivery of the stimulation therapy) may be monitored to determine a characteristic of a washout period, such as a duration of the washout period, an amplitude of the physiological signal waveform during the washout period, a trend in the physiological signal waveform during the washout period, a power level of the physiological signal measured in a particular frequency band of the physiological signal waveform, ratios of power levels between different frequency bands, and the like.

A washout period includes the period of time following delivery of therapy to a patient during which a carryover effect from the therapy delivery dissipates. In the case of electrical stimulation therapy, the carryover effect generally refers to a physiological effect generated in response to the delivery of an electrical stimulation signal, where the effect persists after termination of the stimulation signal. Accordingly, at the end of the washout period, any physiological effects from the delivery of electrical stimulation therapy to the patient are substantially absent. Carryover effects from delivery of therapy may be automatically determined based on one or more physiological parameters of the patient, which are monitored during the delivery of therapy and after the cessation of therapy delivery (i.e., the "post-stimulation" period) with the aid of sensing module 26. The physiological parameters may include, for example, at least one of brain activity (e.g., EEG or ECoG), heart rate, respiratory rate, electrodermal activity (e.g., skin conductance level or galvanic skin response), muscle activity (e.g., via an electromyogram (EMG)), thermal sensing (e.g. to detect facial flushing), cardiac Q-T interval or an activity level of patient 14 (e.g., determined based on a signal from an accelerometer or a piezoelectric crystal).

The heart rate and respiratory rate may be determined by measuring the heart rate and respiratory rate at any suitable place on the patient's body, and need not be directly measured from the heart or lungs. The electrodermal and thermal activity of patient 14 may be measured at the patient's face or any other suitable place on the patient's body, such as on the patient's hands (e.g., the palms), arms, legs, torso, neck, and the like. Thermal activity may indicate, for example, the temperature of the patient's skin due to skin flushing or an increase in blood flow. Monitoring the patient's muscle activity may detect changes to the patient's demeanor, such as changes to the patient's facial features (e.g., by detect facial contraction), tensing of the patient's neck and should muscles, clenching of the patient's hands, and the like, which may indicate a change in the patient's symptoms and/or mood state.

A cardiac Q-T interval is a measure of the time between the start of the Q wave of the heart's electrical cycle and the end of the T wave, and is typically dependent upon the heart rate. Respiratory rate, heart rate, electrodermal activity, facial flushing, and cardiac Q-T interval signals may each be indicative of the patient's anxiety level. For example, a relatively high respiratory rate, heart rate, electrodermal activity, facial flushing, and Q-T interval may be indicative of a relatively high anxiety level of patient 14.

As described in U.S. Pat. No. 9,333,350 to Rise et al. and U.S. Provisional Application No. 61/046,210 to Rise et al., characteristics of the one or more physiological signals during the washout period may be useful for determining a patient mood state during the washout period. The patient mood state may be a symptom of a psychiatric disorder with which the patient is afflicted. For example, a particular waveform trend or waveform amplitude of the physiological signal may be associated with a particular patient mood state, such as an anxious state, a depressive state, and the like. Thus, the monitored signal during the washout period may be compared to the trend template or amplitude threshold value to determine the patient mood state. The probability of the mood state occurring during therapy delivery based on the therapy program may be determined based on the determined patient mood state associated with a therapy program.

Sensing module 26 may be external to patient 14 or may be implanted within patient 14. Sensing module 26 is shown schematically in FIG. 1. Sensing module 26 may be external to patient 14, may be implanted within patient 14 or may include portions both implanted and external to patient 14. In some embodiments, sensing module 26 may be incorporated in a common housing with IMD 16, may include electrodes on an outer housing of IMD 16 or may be coupled to IMD 16 via leads 20 or separate leads.

In some embodiments, sensing module 26 includes electrodes positioned on the patient's face in order to detect the electrical potential generated by the patient's facial muscle cells when the patient's face contracts. That is, in some embodiments, sensing module 26 may include one or more electrodes positioned to detect EMG signals, which may indicate changes to the patient's facial expressions. Certain EMG signals may be associated with particular facial expressions, e.g., during a learning process. In some embodiments, sensing module 26 may include one or more thermal sensing electrodes positioned on the patient's face in order to detect facial flushing. In addition to or instead of the EMG or thermal sensing electrodes, sensing module 26 may include a respiration belt or an electrocardiogram (ECG) belt, as described below with reference to FIG. 6.

IMD 16 includes a therapy module that generates the electrical stimulation delivered to patient 14 via leads 20. In the embodiment shown in FIG. 1, IMD 16 generates the electrical stimulation according to one or more therapy parameters, which may be arranged in a therapy program (or a set of therapy parameter values). In particular, a signal generator (not shown), within IMD 16 produces the stimulation in the manner defined by the therapy program or group of programs selected by the clinician and/or patient 14. The signal generator may be configured to produce electrical pulses to treat patient 14. In other embodiments, the signal generator of IMD 16 may be configured to generate a continuous wave signal, e.g., a sine wave or triangle wave. In either case, IMD 16 generates the electrical stimulation therapy for DBS according to therapy parameter values defined by a particular therapy program.

A therapy program defines values for a number of parameters that define the stimulation. For example, the therapy parameters may include voltage or current pulse amplitudes, pulse widths, pulse rates, pulse frequencies, electrode combinations, and the like. IMD 16 may store a plurality of programs. In some cases, the one or more stimulation programs are organized into groups, and IMD 16 may deliver stimulation to patient 14 according to a program group. For example, IMD 16 may deliver stimulation signals defined by the different therapy programs of the group substantially simulataneously or in an interleavced or alternating manner. The time interval between subsequent stimulation signals may be selected such that patient 14 perceives substantially continuous therapy from delivery of the interleaving of alternating signals.

During a trial stage in which IMD 16 is evaluated to determine whether IMD 16 provides efficacious therapy to patient 14, the stored programs may be tested and evaluated for efficacy. IMD 16 may include a memory to store one or more therapy programs (e.g., arranged in groups), and instructions defining the extent to which patient 14 may adjust therapy parameters, switch between programs, or undertake other therapy adjustments. Patient 14 may generate additional programs for use by IMD 16 via patient programmer 24 at any time during therapy or as designated by the clinician.

Generally, an outer housing of IMD 16 is constructed of a biocompatible material that resists corrosion and degradation from bodily fluids. The outer housing of IMD 16 may substantially enclose the therapy module, processor, memory and other components of IMD 16, e.g., via a hermetic housing. IMD 16 may be implanted within a subcutaneous pocket close to the stimulation site. Although IMD 16 is implanted within a chest cavity of patient 14 in the embodiment shown in FIG. 1, in other embodiments, IMD 16 may be implanted within cranium. In addition, while IMD 16 is shown as implanted within patient 14 in FIG. 1, in other embodiments, IMD 16 may be located external to the patient. For example, IMD 16 may be a trial stimulator electrically coupled to leads 20 via a percutaneous lead during a trial period. If the trial stimulator indicates therapy system 10 provides effective treatment to patient 14, the clinician may implant a chronic stimulator within patient 14 for long term treatment.

Clinician programmer 22 may be a computing device including, for example, a personal digital assistant (PDA), a laptop computer, a desktop PC, a workstation, and the like that permits a clinician to program electrical stimulation therapy for patient 14, e.g., using input keys and a display. For example, using clinician programmer 22, the clinician may specify therapy programs that include one or more therapy parameter values and/or organize the therapy programs into therapy program groups (i.e., groups including one or more therapy parameters) for use in delivery of DBS. Clinician programmer 22 supports telemetry (e.g., radio frequency (RF) telemetry) with IMD 16 to download stimulation parameters and, optionally, upload operational or physiological data stored by IMD 16. In this manner, the clinician may periodically interrogate IMD 16 to evaluate efficacy and, if necessary, modify the stimulation parameters.

Like clinician programmer 22, patient programmer 24 may be a handheld computing device. Patient programmer 24 may also include a display and input keys to allow patient 14 to interact with patient programmer 24 and IMD 16. In this manner, patient programmer 24 provides patient 14 with an interface for limited control of electrical stimulation therapy provided by IMD 16. For example, patient 14 may use patient programmer 24 to start, stop or adjust electrical stimulation therapy. In particular, patient programmer 24 may permit patient 14 to adjust stimulation parameters such as duration, amplitude, pulse width and pulse rate within an adjustment range specified by the clinician via clinician programmer 22, select from a library of stored stimulation therapy programs, or reset the current therapy cycle.

Patient programmer 24 includes input mechanisms to allow patient 14 to enter information related to a patient event or symptom of a psychiatric disorder. For example, any of the above-listed input mechanisms may be used to enter information including, but not limited to, information indicating the presence, and, in some cases, the severity, of a particular mood state or psychiatric disorder symptom. The information entered by patient 14 may be associated with the specific therapy program.

Clinician programmer 22 may be used to program and/or interrogate IMD 16 and patient programmer 24, as described in further detail below. IMD 16, clinician programmer 22, and patient programmer 24 may communicate via cables or a wireless communication, as shown in FIG. 1. Clinician programmer 22 and patient programmer 24 may, for example, communicate via wireless communication with IMD 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 2:
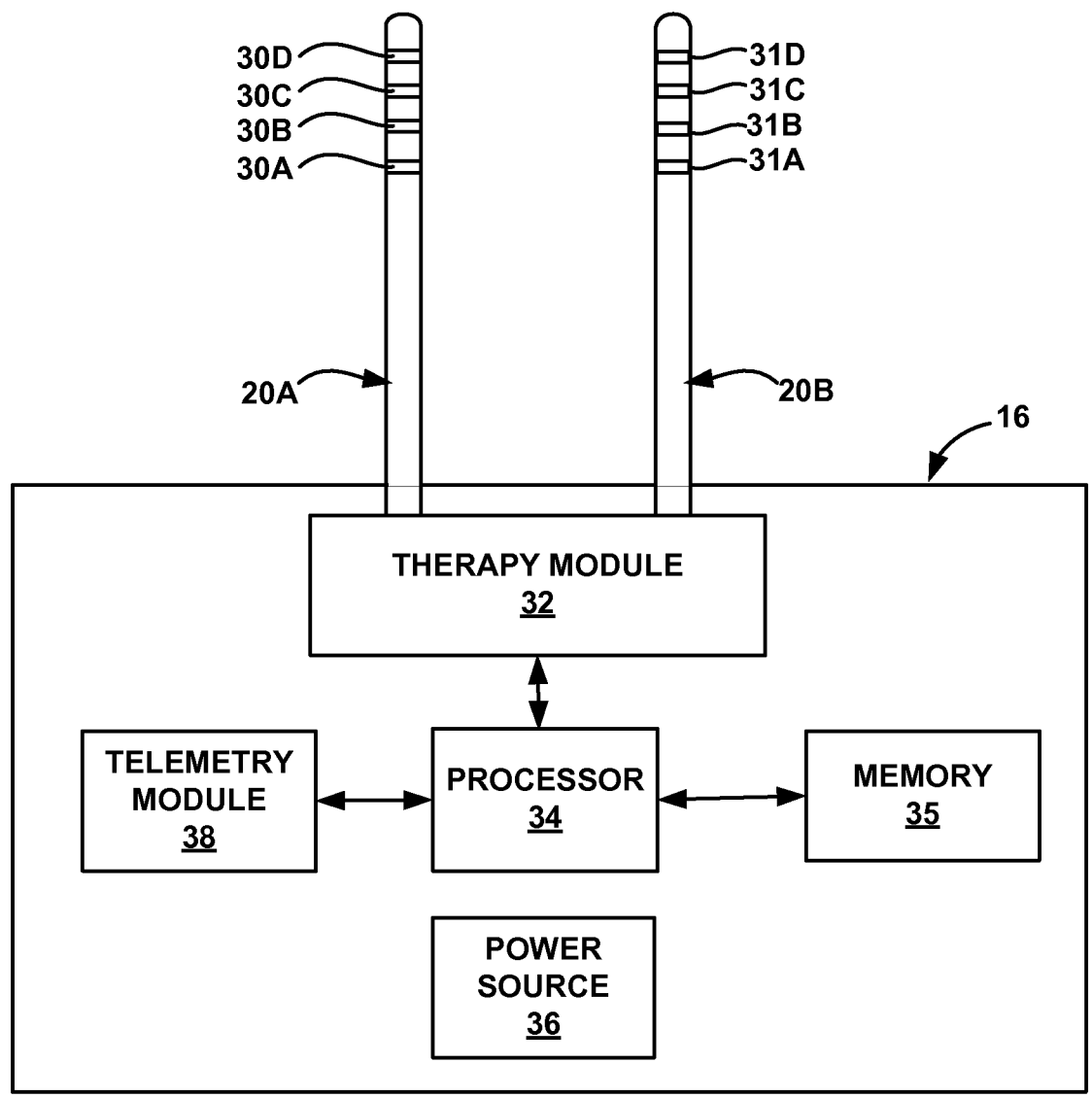
FIG. 2 is a schematic block diagram illustrating components of an example medical device.

FIG. 2 is a functional block diagram illustrating components of an example IMD 16 in greater detail. IMD 16 is coupled to leads 20A and 20B, which include electrodes 30A-30D and 31A-30D, respectively. Although IMD 16 is coupled directly to leads 20, in other embodiments, IMD 16 may be coupled to leads 20 indirectly, e.g., via lead extension 18 (FIG. 1). IMD 16 includes therapy module 32, processor 34, memory 35, power source 36, and telemetry module 38.

IMD 16 may deliver electrical stimulation therapy to brain 12 of patient 14 via electrodes selected from among electrodes 30A-30D of lead 20A and electrodes 31A-30D of lead 20B (collectively "electrodes 30 and 31"). In the embodiment shown in FIG. 2, implantable medical leads 20 are substantially cylindrical, such that electrodes 30, 31 are positioned on a rounded outer surface of leads 20. As previously described, in other embodiments, leads 20 may be, at least in part, paddle-shaped (i.e., a "paddle" lead). In some embodiments, electrodes 30, 31 may be ring electrodes. In other embodiments, electrodes 30, 31 may be segmented or partial ring electrodes, each of which extends along an arc less than 360 degrees (e.g., 90-120 degrees) around the outer perimeter of the respective lead 20. The use of segmented or partial ring electrodes 30, 31 may also reduce the overall power delivered to electrodes 30, 31 by IMD 16 because of the ability to more efficiently deliver stimulation to a target stimulation site by eliminating or minimizing the delivery of stimulation to unwanted or unnecessary regions within patient 14.

The configuration, type, and number of electrodes 30, 31 illustrated in FIG. 2 are merely exemplary. For example, in other examples, IMD 16 may be coupled to a single lead with eight electrodes on the lead or three or more leads with the aid of bifurcated lead extensions. Electrodes 30, 31 are electrically coupled to a therapy module 32 of IMD 16 via conductors within the respective leads 20A, 20B. Each of electrodes 30, 31 may be coupled to separate conductors so that electrodes 30, 31 may be individually selected, or in some embodiments, two or more electrodes 30 and/or two or more electrodes 31 may be coupled to a common conductor. In one embodiment, an implantable signal generator or other stimulation circuitry within therapy module 32 delivers electrical signals to a target tissue site within patient 14 via at least some of electrodes 30, 31 under the control of processor 34. The stimulation energy generated by therapy module 32 may be delivered from therapy module 32 to selected electrodes 30, 31 via a switching module and conductors carried by leads 16, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like, and the functions attributed to processor 34 may be embodied as software, firmware, hardware or any combination thereof. The functions attributed to processors described herein may be embodied in a hardware device via software, firmware, hardware or any combination thereof.

Processor 34 controls the implantable signal generator within therapy module 32 to deliver electrical stimulation therapy according to selected therapy parameters. Specifically, processor 34 controls therapy module 32 to deliver electrical signals with selected voltage or current amplitudes, pulse widths (if applicable), and rates specified by one or more therapy programs, which may be arranged into therapy program groups. In one embodiment, processor 34 controls therapy module 32 to deliver stimulation therapy according to one therapy program group at a time. The therapy programs may be stored within memory 35. In another embodiment, therapy programs are stored within at least one of clinician programmer 22 or patient programmer 24, which transmits the therapy programs to IMD 16 via telemetry module 38.

In addition, processor 34 may also control therapy module 32 to deliver the electrical stimulation signals via selected subsets of electrodes 30, 31 with selected polarities. For example, electrodes 30, 31 may be combined in various bipolar or multi-polar combinations to deliver stimulation energy to selected sites, such as sites within brain 12. The above-mentioned switching module may be controlled by processor 34 to configure electrodes 30, 31 in accordance with a therapy program. However, in some examples, processor 34 may configure electrodes 30, 31 without the aid of switching modules.

In embodiments in which IMD 16 senses a patient parameter, such as an EEG, ECoG, heart rate or respiratory rate of patient 14, processor 34 may control therapy module 32 to sense the patient parameter. The sensed parameter signals generated by therapy module 32 may be stored within memory 35. Memory 35 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 35 may store program instructions that, when executed by processor 34, cause IMD 16 to perform the functions ascribed to IMD 16 herein. In some embodiments, memory 35 may also store the parameters for therapy programs or program groups and/or patient physiological data (such as sensed physiological signals) obtained by IMD 16 or another sensing module.

During a trial session, which may occur after implantation of IMD 16 or prior to implantation of IMD 16 within patient 14, a clinician may determine the therapy parameter values of therapy programs that provide efficacious therapy to patient 14. Processor 34 may control therapy module 32 based on information provided by clinician programmer 22, patient programmer 24 or another computing device. For example, the clinician may interact with clinician programmer 22 to select a particular therapy program and clinician programmer 22 may transmit a control signal to IMD 16, which is received by telemetry module 38 of IMD 16. The control signal may cause processor 34 to control therapy module 32 to deliver therapy based on the parameter values specific by the clinician-selected therapy program. As another example, clinician programmer 22, patient programmer 24 or another computing device may utilize a search algorithm that automatically selects therapy programs for trialing.

Figure 3:
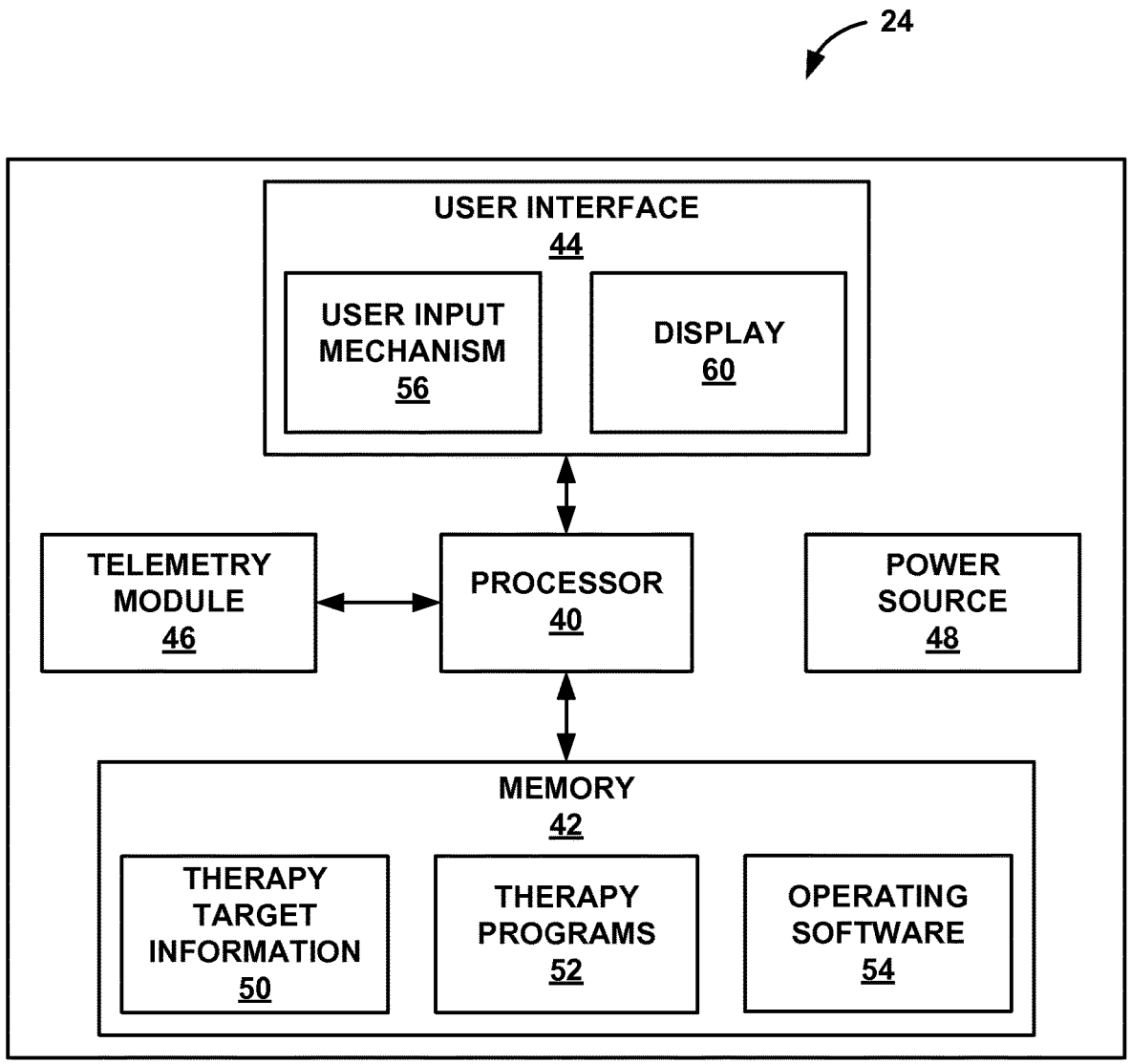
FIG. 3 is a schematic block diagram illustrating components of an example patient programmer.

FIG. 3 is a functional block diagram illustrating components of an example patient programmer 24, which includes processor 40, memory 42, user interface 44, telemetry module 46, and power source 48. Processor 40 controls user interface 44 and telemetry module 46, and stores and retrieves information and instructions to and from memory 42. Patient programmer 24 may be a dedicated hardware device with dedicated software for programming of IMD 16. Alternatively, patient programmer 24 may be an off-the-shelf computing device running an application that enables programmer 24 to program IMD 16.

Patient 14 may use patient programmer 24 to select therapy programs (e.g., sets of stimulation parameter values), generate new therapy programs, modify therapy programs through individual or global adjustments or transmit the new programs to a medical device, such as IMD 16 (FIGS. 1 and 2). Patient 14 may interact with patient programmer 24 via user interface 44, which includes user input mechanism 56 and display 60. Patient 14 may input information via user interface 44 relating to the therapeutic efficacy of a therapy program, to indicate the presence of a mood state, and/or to input information relating to patient symptoms of a psychiatric disorder in addition to or instead of the mood state.

User input mechanism 56 may include any suitable mechanism for receiving input from patient 14 or another user. In one embodiment, user input mechanism includes an alphanumeric keypad. In another embodiment, user input mechanism 56 includes a limited set of buttons that are not necessarily associated with alphanumeric indicators. For example, the limited set of buttons may include directional buttons that permit patient 14 to scroll up, down, or sideways through a display presented on display 60, select items shown on display 60, as well as enter information. The limited set of buttons may also include "increment/decrement" buttons in order to increase or decrease a stimulation frequency or amplitude of stimulation delivered by IMD 16.

User input mechanism 56 may include any one or more of push buttons, soft-keys (e.g., with functions and contexts indicated on display 60), voice activated commands, activated by physical interactions, magnetically triggered, activated upon password authentication push buttons, contacts defined by a touch screen, or any other suitable user interface. In some embodiments, buttons of user input mechanism 56 may be reprogrammable. That is, during the course of use of patient programmer 24, the buttons of user input mechanism 56 may be reprogrammed to provide different programming functionalities as the needs of patient 14 change or if the type of IMD 16 implanted within patient 14 changes. User input mechanism 56 may be reprogrammed, for example, by clinician programmer 22 (FIG. 1) or another computing device.

Display 60 may include a color or monochrome display screen, such as a liquid crystal display (LCD), light emitting diode (LED) display or any other suitable type of display. Patient programmer 24 may present information related to stimulation therapy provided by IMD 16, as well as other information, such as historical data regarding the patient's condition and past mood state or other symptom information. Processor 46 monitors activity from user input mechanism 56, and controls display 60 and/or IMD 16 function accordingly. In some embodiments, display 60 may be a touch screen that enables the user to select options directly from the display. In such cases, user input mechanism 56 may be eliminated, although patient programmer 24 may include both a touch screen and user input mechanism 56. In some embodiments, user interface 44 may also include audio circuitry for providing audible instructions or sounds to patient 14 and/or receiving voice commands from patient 14.

User interface 44 may also include an LED or another indication (e.g., via display 60) that provides confirmation to patient 14 that an operation was carried out or that information input via user input mechanism 56 was received. After patient 14 provides input regarding patient symptoms or to indicate the occurrence of a depressive or manic episode, user interface 44 may activate an LED to provide positive feedback to patient 14 regarding the successfully received information.

Processor 40 may comprise any combination of one or more processors including one or more microprocessors, DSPs, ASICs, FPGAs, or other equivalent integrated or discrete logic circuitry. Accordingly, processor 40 may include any suitable structure, whether in hardware, software, firmware, or any combination thereof, to perform the functions ascribed herein to processor 40. Memory 42 may include any volatile or nonvolatile memory, such as RAM, ROM, EEPROM or flash memory. Memory 42 may also include a removable memory portion that may be used to provide memory updates or increases in memory capacities. A removable memory may also allow patient data to be easily transferred to clinician programmer 22, or to be removed before patient programmer 24 is used by a different patient. Memory 42 stores, among other things, therapy target information 50, therapy programs 52, and operating software 54. Memory 42 may have any suitable architecture. For example, memory 42 may be partitioned to store therapy target information 50, therapy programs 52, and operating software 54. Alternatively, therapy target information 50, therapy programs 52, and operating software 54 may each include separate memories that are linked to processor 40.

Therapy target information 50 portion of memory 42 stores data relating to the target sites within patient 14 for therapy delivery. In the DBS example illustrated in FIG. 1, the therapy target information 50 may identify various brain structures for therapy delivery. In addition, as described in further detail below, therapy target information 50 may include information associating patient symptoms or mood states with therapy targets that are believed to manage the symptoms or mood states. Therapy for managing a particular patient symptom or mood state may be more efficacious when IMD 16 delivers therapy to one target tissue site within patient 14 compared to another target tissue site. Data stored within therapy target information 50 may store these relationships between target tissue sites and patient symptoms and/or mood states. The information may be specific to patient 14 or may be general to more than one patient, e.g., general to a class of patients having similar patient symptoms or mood states.

Target sites for therapy delivery may be associated with particular electrodes on leads 20 (FIG. 1) based on estimated or actual locations of electrodes following implant. The estimated locations of electrodes may be based on an anatomical atlas of brain 12 that is specific to patient 14 or general to more than one patient, or may be based on a rough estimation of the location of leads 20 based on estimated implant location (e.g., based on the stereotactic data). A stereotactic frame may be placed on a cranium of patient 14 to specifically locate areas of brain 12. In addition, this stereotactic information may be used to provide coordinates of the location of implanted leads 20. An actual location of the electrodes 30, 31 (FIG. 2) of leads 20 may be based on medical imaging of brain 12 after leads 20 are implanted, e.g., via fluoroscopy or another suitable imaging technique.

Therapy programs 52 portion of memory 42 stores data relating to the therapy programs implemented by IMD 16. In some embodiments, the actual settings for the therapy programs, e.g., the stimulation amplitude, pulse rate, pulse frequency and pulse width data, are stored within therapy programs 52. In other embodiments, an indication of each therapy program or group of therapy programs, e.g., a single value associated with each therapy program or group, may be stored within therapy programs 52, and the actual parameters may be stored within memory 35 (FIG. 2) of IMD 16. The "indication" for each therapy program or group may include, for example, alphanumeric indications (e.g., Therapy Program Group A, Therapy Program Group B, and so forth), or symbolic indications.

Operating software 54 may include instructions executable by processor 40 for operating user interface 44, telemetry module 46 and managing power source 48. Memory 42 may also store any therapy data retrieved from IMD 16 during the course of therapy. The clinician may use this therapy data to determine the progression of the patient's condition in order to predict or plan a future treatment.

Patient programmer 24 may communicate via wireless telemetry with IMD 16, such as using RF communication or proximal inductive interaction. This wireless communication is possible through the use of telemetry module 46. Accordingly, telemetry module 46 may be similar to the telemetry module contained within IMD 16. Telemetry module 46 may also be configured to communicate with clinician programmer 22 or another computing device via wireless communication techniques, or direct communication through a wired connection. Examples of local wireless communication techniques that may be employed to facilitate communication between patient programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 24 without needing to establish a secure wireless connection.

Power source 48 delivers operating power to the components of patient programmer 24. Power source 48 may include a battery and a power generation circuit to produce the operating power. In some embodiments, the battery may be rechargeable to allow extended operation. Recharging may be accomplished electrically coupling power source 48 to a cradle or plug that is connected to an alternating current (AC) outlet. In addition, recharging may be accomplished through proximal inductive interaction between an external charger and an inductive charging coil within patient programmer 24. In other embodiments, traditional batteries (e.g., nickel cadmium or lithium ion batteries) may be used. In addition, patient programmer 24 may be directly coupled to an alternating current outlet recharge power source 48, or to power patient programmer 24. Power source 48 may include circuitry to monitor power remaining within a battery. In this manner, user interface 44 may provide a current battery level indicator or low battery level indicator when the battery needs to be replaced or recharged. In some cases, power source 48 may be capable of estimating the remaining time of operation using the current battery.

Figure 4:
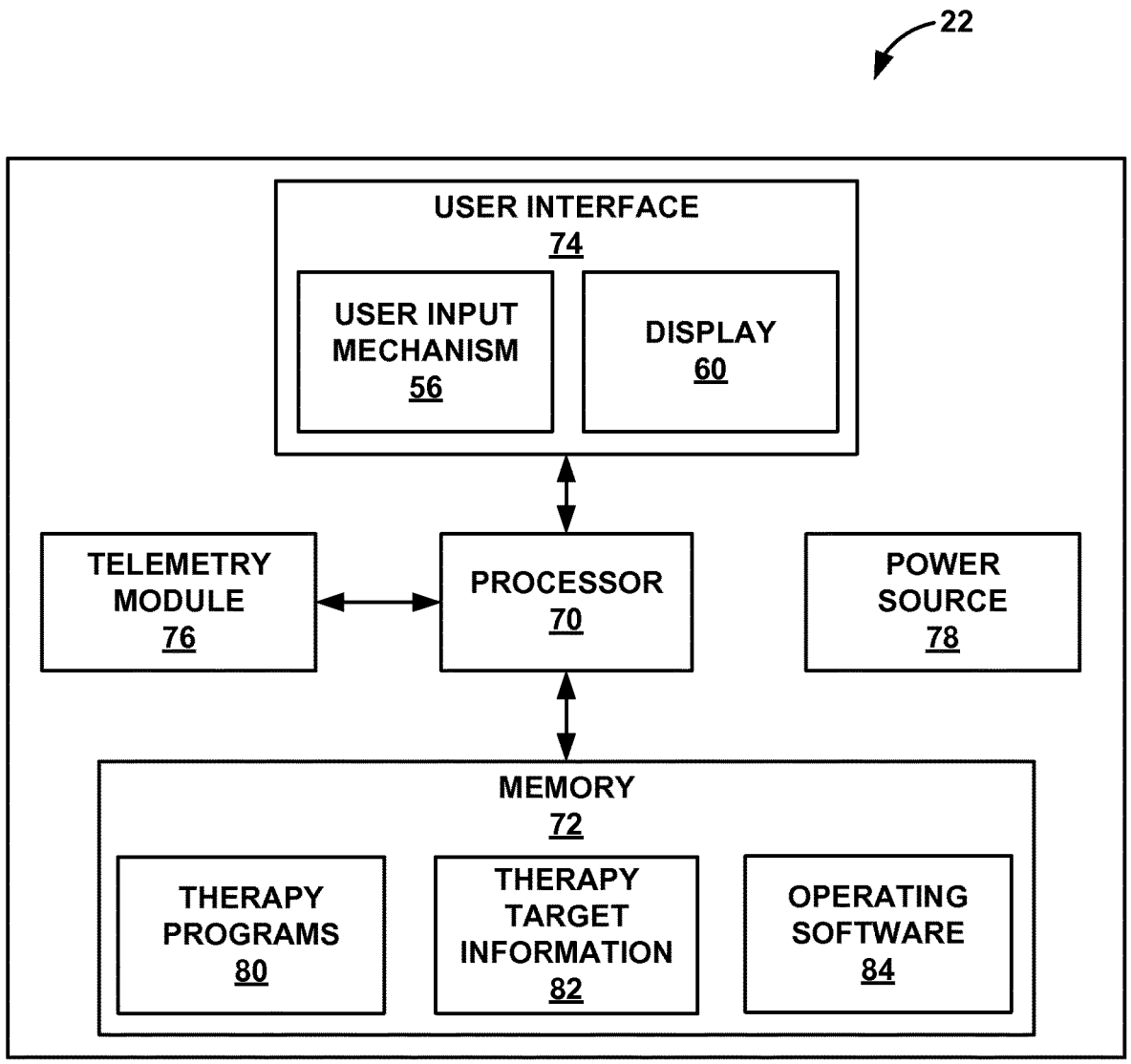
FIG. 4 is a schematic block diagram illustrating components of an example clinician programmer.

FIG. 4 is a functional block diagram illustrating components of an example clinician programmer 22, which may be similar to the components of patient programmer 24. In the example shown in FIG. 4, clinician programmer 22 includes processor 70, memory 72 including therapy programs 80, target therapy information 82, and operating software 84, user interface 74 including user input mechanism 56 and display 60, telemetry module 76, and power source 78. The functions performed by each component may be similar to the functions described above with reference to the like-components of patient programmer 24.

Clinician programmer 22 may include more features than patient programmer 24. For example, while clinician programmer 22 may be configured for more advanced programming features than patient programmer 24. This may allow a user to modify more therapy parameters with clinician programmer than with patient programmer 24. Patient programmer 24 may have a relatively limited ability to modify therapy parameters of IMD 16 in order to minimize the possibility of patient 14 selecting therapy parameters that are harmful to patient 14. Similarly, clinician programmer 22 may conduct more advanced diagnostics of IMD 16 than patient programmer 24.

As described in further detail below, processor 70 of clinician programmer 22 may interrogate IMD 16 and/or patient programmer 24 to retrieve any collected information stored within memories 35, 42, respectively, such as information relating to a mood state episodes or patient symptoms. The information relating to mood state episodes or patient symptoms may include, for example, a history or pattern of patient symptoms, the severity or duration of the symptoms, the contemporaneous occurrence of symptoms or mood states, and the like. For example, memory 72 of clinician programmer 22 may include software including instructions that cause processor 70 of clinician programmer 22 to interrogate IMD 16 and/or patient programmer 24.

In general, during a programming session, a clinician may select values for a number of programmable therapy parameters in order to define the electrical stimulation therapy to be delivered by IMD 16 to patient 14. For example, the clinician may select a combination of electrodes carried by one or more implantable leads, and assigns polarities to the selected electrodes. In addition, the clinician may select an amplitude, which may be a current or voltage amplitude, a pulse width, and a pulse rate, in the case of an IMD 16 that delivers stimulation pulses to patient 14. A group of parameter values, including electrode configuration (electrode combination and electrode polarity), amplitude, pulse width and pulse rate, may be referred to as a therapy program in the sense that they drive the neurostimulation therapy to be delivered to the patient.

Programs selected during a programming session using clinician programmer 22 may be transmitted to and stored within one or both of patient programmer 24 and IMD 16. Where the programs are stored in patient programmer 24, patient programmer 24 may transmit the programs selected by patient 14 to IMD 16 for delivery of neurostimulation therapy to patient 14 according to the selected program. Where the programs are stored in IMD 16, patient programmer 24 may receive a list of programs from IMD 16 to display to patient 14, and transmit an indication of the selected program to IMD 16 for delivery of neurostimulation therapy to patient 14 according to the selected program.

During a programming session, which may also be referred to as a therapy program trial session, the clinician may specify a program using clinician programmer 22 by selecting values for various therapy parameters. When a program is specified, the clinician may test the program by directing clinician programmer 22 to control IMD 16 to deliver therapy according to the program to patient 14. During the programming session, multiple therapy programs may be tested. The clinician or patient may enter rating information into clinician programmer 22 for each tested program. The rating information for a tested program may include information relating to effectiveness of delivery of stimulation therapy according to the program in treating symptoms or alleviating a mood state episode of the patient, side effects experienced by the patient due to the delivery of stimulation therapy according to the program, or both. In the case of psychiatric disorder stimulation therapy, efficacy information may include an indication of patient mood state during therapy delivery and during a washout period following therapy delivery. The patient mood state information may include, for example, patient feedback (received via patient programmer 24) and/or physiological parameter values that are associated with a particular patient mood state.

Figures 5, 6:
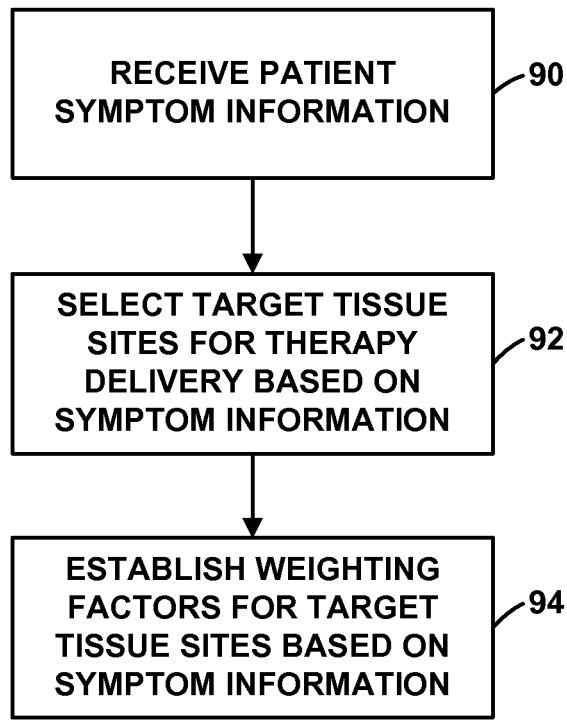
FIG. 5 is a flow diagram illustrating an example technique for selecting the target tissue sites for therapy delivery and establishing weighting factors for the target tissue sites.
FIG. 6 is a schematic illustration of an example data structure that associates symptoms of a psychiatric disorder with target tissue sites within a brain.

As previously discussed, IMD 16 delivers therapy to two or more different target tissue sites within patient 14. In the example shown in FIG. 1, IMD 16 delivers electrical stimulation to two or more targets within brain 12. For example, electrodes 30, 31 of leads 20 may be positioned to deliver electrical stimulation to the CG25 and VC/VS, respectively, of brain 12. The therapy targets may be selected based upon patient symptoms. In addition, in some examples, therapy delivery to the two or more target tissue sites may be controlled based on respective weighting factors for the target tissue sites. FIG. 5 is a flow diagram illustrating an example technique for selecting the target tissue sites for the therapy delivery and establishing weighting factors for the target tissue sites. While processor 70 of clinician programmer 22 is primarily referred to in the description of FIG. 5, in other embodiments, processor 34 of IMD 16, processor 40 of patient programmer 24 or a processor of another device may select target tissue sites and apply weighting factors to the target tissue sites in accordance with the technique shown in FIG. 5.

In accordance with the technique shown in FIG. 5, processor 70 receives information relating to patient symptoms (90). The patient symptoms may be related to the psychiatric disorder for which therapy system 10 is implemented to manage. The symptoms of a depressive disorder, such as major depressive disorder (MDD), may include, for example, fatigue, anhedonia, depressed mood, loss of energy, diminished ability to think or concentrate, indecisiveness, or recurrent thoughts of death or suicidal ideation, insomnia or hypersomnia. As an example, the patient symptoms may be defined by the Diagnostic and Statistical Manual of Mental Disorders (DSM-IV), which is a book, published by the American Psychiatric Association, which defines criteria used to diagnose various mental disorders, including depression.

As provided in the Diagnostic and Statistical Manual of Mental Disorders (DSM-IV), criteria for detecting an episode of MDD include the presence of either depressed mood or anhedonia in addition to four other symptoms within the same two week period. The symptoms include, for example, (1) depressed mood for most of the day and nearly every day; (2) anhedonia (diminished interest or pleasure in all or almost all activities most of the day and nearly every day; (3) significant weight loss when not dieting or weight gain, or a decrease in appetite, (4) insomnia or hypersomnia nearly every day; (5) psychomotor agitation (e.g., pacing around a room, writing one's hands, or other unintentional and purposeless motions) or retardation (e.g., feeling slowed down) nearly every day; (6) fatigue or loss of energy nearly every day; (7) feelings of worthlessness or excessive or inappropriate guilty nearly every day; (8) diminished ability to think or concentrate, or indecisiveness nearly every day, and (9) recurrent thoughts of death or suicidal ideation without a specific plan, or a suicide attempt or specific plan. The Diagnostic and Statistical Manual of Mental Disorders (DSM-IV) provides other criteria for MDD. Any one or more of these symptoms of a MDD episode may be used to detect a depressive mood state. Further, any one or more of these symptoms may be a symptom of a psychiatric disorder that is used to select a target therapy site.

As provided in the Diagnostic and Statistical Manual of Mental Disorders (DSM-IV), criteria for a manic episode, which may indicate the presence of a psychiatric disorder, include a distinct period of abnormally and persistently elevated, expansive or irritable mood, lasting at least one week. In addition, the criteria include the presence of three or more of the following symptoms during the period of mood disturbance: (1) inflated self-esteem or grandiosity; (2) decreased need for sleep; (3) more talkative than usual or pressure to keep talking; (4) flight of ideas or subjective experience that thoughts are racing; (5) distractibility; (6) increase in goal-directed activity or psychomotor agitation; and (7) excessive involvement in pleasurable activities that have a high potential for painful consequences. The Diagnostic and Statistical Manual of Mental Disorders (DSM-IV) provides other criteria for diagnosing a manic episode. Any one or more of these symptoms of a manic episode may be used to detect a manic mood state. Further, any one or more of these symptoms may be a symptom of a psychiatric disorder that is used to select a target therapy site.

As provided in the Diagnostic and Statistical Manual of Mental Disorders (DSM-IV), criteria for a mixed episode, which may indicate the presence of a psychiatric disorder, include both the symptoms and criteria for the manic episode and MDD listed above.

In addition, the Diagnostic and Statistical Manual of Mental Disorders (DSM-IV), provides criteria for a hypomanic episode, which may indicate the presence of a psychiatric disorder. A hypomanic episode may be characterized by the presence of a distinct period of persistently elevated, expansive or irritable mood, lasting throughout at least four days, and is clearly different from a typical nondepressed mood for the patient, as well as the presence of three or more of the following symptoms within the period (or four or more if the patient was in an irritable mood): (1) inflated self-esteem or grandiosity; (2) decreased need for sleep; (3) more talkative than usual or pressure to keep talking; (4) flight of ideas or subjective experience that thoughts are racing; (5) distractibility; (6) increase in goal-directed activity or psychomotor agitation; and (7) excessive involvement in pleasurable activities that have a high potential for painful consequences. A hypomanic episode may be less severe than a manic episode. These symptoms may also be used to diagnose a hypomanic mood state.

In some embodiments, processor 70 may receive patient symptom information (90) from a user, such as patient 14 or a clinician, via user input mechanism 56 or display 60 of user interface 44 of patient programmer 24 (FIG. 3). For example, when a symptom occurs, patient 14 may provide input via user interface 44. Patient 14 may indicate the occurrence of a patient symptom and the type of patient symptom using any suitable technique. In one embodiment, patient 14 merely indicates the occurrence of a particular type of symptom. For example, user interface 44 of clinician programmer 22 may include a plurality of buttons dedicated to recording the time and date of the occurrence of different symptoms, and patient 14 may depress the relevant dedicated button. Alternatively, a multifunction button may be used in combination with a particular user interface display to indicate the occurrence of a particular type of patient symptom. As another example, user interface 44 of clinician programmer 22 may present a graphical display that presents a list of symptoms, and patient 14 may select one or more symptoms from the predefined list upon experiencing the symptoms. Alternatively, patient 14 may manually input information identifying the type of patient symptom upon occurrence of the symptom.

In some embodiments, patient 14 may also provide information regarding the severity of the patient symptom. For example, patient 14 may select a numerical rating of the severity of the symptom (e.g., a numerical range of 1 through 10, where 10 indicates a severe rating). In other embodiments, processor 70 may automatically rate the severity of the patient symptoms based on patient responses to various questions that are specific to the symptoms, and by be a part of one or more validated questionnaires, such as the Beck Depression Inventory, Hamilton Rating Scale for Depression (HAM-D) or the Montgomery-Asberg Depression Rating Scale (MADRS). The Beck Depression Inventory and the HAM-D are both 21-question multiple choice surveys that is filled out by patient 14, and the MADRS is a ten-item questionnaire. The patient input for each of the questions of the questionnaires may be received by patient programmer 24 and transmitted to processor 70 of clinician programmer 22, or may be directly received by processor 70. Processor 70 may use other techniques for receiving input regarding symptoms of patient 14.

Processor 70 selects the target tissue sites based on the patient symptoms (92). Different patient symptoms may be associated with different structures within brain 12, and, in some cases, different regions of the same structure. That is, therapy delivery to one region of brain 12 may provide relatively efficacious therapy for a first patient symptom (e.g., by mitigating the severity, decreasing the duration or eliminating the symptom), but therapy delivery to the same region of brain 12 may provide little to no efficacy in managing a second patient symptom that is different than the first patient symptom. Managing a patient symptom may include, for example, reducing the severity or duration of the patient symptom, and, in some cases, eliminating the occurrence of the symptom. For example, stimulation of one target tissue site within brain 12 may increase the patient's interoception of energy, thereby improving the patient's fatigue and loss of energy feelings. However, stimulation of that same target may not improve the patient's anhedonia.

A single patient symptom may be associated with two or more target tissue sites, and a common target tissue site may be used to address more than one patient symptom. Processor 70 may reference therapy target information 82 stored in memory 72 (FIG. 4) to determine the brain structures with which the patient symptoms are associated in order to select the target tissue sites. In some embodiments, processor 70 selects target tissue sites that are associated with the two patient symptoms that have the highest severity rating compared to the other patient symptoms. However, in other embodiments, processor 70 selects target tissue sites for managing all the existing patient symptoms.

Examples of different relationships between patient symptoms and target tissue sites of brain 12 are described below with respect to FIG. 6. In some embodiments, processor 70 may reference a data structure, such as the one shown in FIG. 6, to select the target tissue sites based on the symptom information (92). FIG. 6 illustrates a table that associates patient symptoms of MDD with target tissue sites within brain 12. The target tissue sites may be sites within brain 12 that are closely related to the respective patient symptoms, such that delivery of electrical stimulation to the target tissue site helps to alleviate the severity or even eliminate the occurrence of the respective patient symptom.

The target tissue sites may be identified and associated with the patient symptoms using any suitable technique. For example, the target tissue sites may be identified with the aid of functional medical imaging techniques, such as position emission tomography (PET), magnetic resonance imaging (MRI), functional MRI (fMRI), and magnetoencephalography (MEG). Patient input regarding symptoms may be received as the medical image is generated, and the clinician may identify the target tissue sites that are associated with the indicated symptoms based on data provided by the medical image.

In other embodiments, the target tissue sites may be identified by delivering test therapy (e.g., electrical stimulation or a therapeutic agent) to different target tissue sites within brain 12 and determining which, if any, patient symptoms are mitigated in response to the delivery of therapy. Improvements to the patient's symptoms may be assessed, for example, using the Brief Affect Scale (BAS), which measures change in mood state based on a seven-point scale. If, for example, the patient's depressed mood is improved in response to delivery of electrical stimulation to the VC/VS, the clinician may associate the depressed mood symptom with the VC/VS in therapy target information portion 82 of memory 72 (FIG. 4). In some cases, the test therapy delivery and symptom association techniques may be performed during a trial period, prior to implementation of IMD 16 on a chronic (e.g., nontemporary) basis. In other cases, the test therapy delivery and symptom association techniques may be performed after IMD 16 is implanted within patient 14.

As FIG. 6 illustrates, a target tissue site may be associated with more than one patient symptom. In one example, the VC/VS may be associated with symptoms of fatigue, anhedonia, and loss of energy. In addition, two or more patient symptoms may be associated with the same target tissue site. As shown in the example in FIG. 6, a patient symptom may also be associated with two or more target tissue sites. In the example shown in FIG. 6, depressed mood is associated with the CG25 and Brodmann Area 10 region of the cortex. In other embodiments, one psychiatric disorder symptom may be associated with a single tissue site.

In one example, based on the information provided in FIG. 6, for a patient whose dominant symptom of a depressed state is anhedonia with a sense of fatigue, but otherwise has a less severe depressed mood, processor 70 may assign a stronger weight to the VC/VS tissue site for purposes of therapy delivery. As a result, the VC/VS may receive less therapy than Brodmann area 10. In contrast, a patient that experiences significant anxiety as part of their depression may have a higher intensity stimulation delivered to Brodmann Area 11 compared to the VC/VS.

While a table that associates psychiatric disorder symptoms with target tissue sites for therapy delivery is shown in FIG. 6, in other embodiments, other types of data structures may be stored within memory 72 of clinician programmer 22 or a memory of another device.

In addition to storing information associating patient symptoms with target tissue sites, memory 72 (or a memory of another device, such as IMD 16 or patient programmer 24) may store information that associates therapy programs with particular patient symptoms. In examples in which IMD 16 delivers electrical stimulation therapy, the therapy programs may specify electrode combinations for delivering stimulation to patient 14. The electrode combinations may specify the specific electrodes selected from an available array of electrodes 30, 31 for delivering stimulation, as well as the polarities (e.g., positive or negative) of the selected electrodes. If leads 20 are positioned such that electrodes 30, 31 extend across more than one target tissue site, specifying the electrode combination may also specify the target tissue site for therapy delivery.

For example, delivery of stimulation by a first set of electrodes may deliver stimulation to a first target tissue site, and deliver of stimulation by a second set of electrodes, which differ in at least one electrode from the first set of electrodes, may deliver stimulation to a second target tissue site within brain 12. The first and second set of electrodes may, for example, have different longitudinal positions relative to a longitudinal axis of leads 20 and/or different lateral positions (e.g., along an outer circumference of a lead 20 having a circular cross-section). Different lateral positions may be achieved if electrodes 30, 31 are segmented or partial-ring electrodes. A therapy program may also specify the other parameters of therapy, such as the voltage or current amplitude, signal duration, and frequency of the signals.

In other embodiments, memory 72 (or a memory of another device) may store information that associates particular therapy programs with particular target therapy sites. In this way, the target therapy sites may be mapped relative to the available array of electrodes 30, 31, thereby enabling processor 70 to select electrodes for stimulation delivery based on the selected target tissue sites.

Returning to FIG. 5, after processor 70 selects target tissue sites, processor 70 establishes weighting factors for the target tissue sites based on the symptom information (94). The weighting factors may indicate the relative importance of a selected target tissue site compared to another selected target tissue site. The relative importance may be determined based on, for example, the relative severity of the symptoms associated with the target tissue sites. For example, processor 70 may apply more weight to a first target tissue site compared to a second target tissue site if the first target tissue site is associated with a severe rating of depressed mood and the second target tissue site is associated with a moderate rating of fatigue.

In another embodiment, processor 70 may weigh the target tissue sites based on the type of patient symptoms associated with the target tissue sites. For example, processor 70 may apply more weight to a first target tissue site compared to a second target tissue site if the first target tissue site is associated with a depressed mood and the second target tissue site is associated with loss of energy. The clinician may provide instructions that, for example, indicate to processor 70 that depressed mood is an absolutely more severe symptom than loss of energy, regardless of the severity rating of the symptoms.

The weighting factors may be used to control therapy delivery. In one embodiment, the weighting factors may indicate the intensity of stimulation delivered to one selected target tissue site over another selected target tissue site. For example, each weighting factor may be associated with a particular absolute intensity of stimulation. In some embodiments, therapy programs portion 80 of memory 72 (FIG. 4) may associate different therapy programs with weighting factors. Each therapy program may be associated with a particular stimulation intensity. Upon determining that a first therapy site is associated with a first weighting factor and a second therapy site is associated with a second weighting factor, processor 70 may reference the stored information in order to determine which therapy programs control therapy to first and second therapy sites based on the first and second weighting factors, respectively.

Intensity of stimulation may be a function of, for example, any one or more of the voltage or current amplitude value of the stimulation signal, frequency of stimulation signals, signal duration (e.g., pulse width in the case of stimulation pulses), signal burst pattern, and the like. The intensity of stimulation may, for example, affect the volume of tissue that is activated by the electrical stimulation. Thus, the clinician may increase the voltage amplitude to cause a larger volume of nervous tissue within a cortical region to be activated. If the nerve cells within that volume are processing information in parallel, then a greater number of nerve cells will be active as the amplitude is increased.

In some embodiments, the weighting factors are based on a scale of 0% to 100% of the maximum therapeutic range for each target tissue site. A weight of 100% indicates applying the maximum therapy allowed for that target. "Maximum" therapy may refer to a combination of current or voltage amplitude and signal duration (e.g., pulse width), which may be used to generally characterize an intensity of stimulation in some embodiments. Stimulation frequency (e.g., pulse frequency) may be a second dimension of the therapy delivery, and duty cycle for a program of cycling stimulation on and off, or between two other states, may be a third dimension of the therapy. In addition, the therapy "on time" may be unique for the target tissue site. For example if therapy delivery to a particular therapy target has an impact on insomnia, IMD 16 may deliver therapy to the therapy target during the entire night or only during a portion of the night if a subject exhibits insomnia in the middle night or early morning only.

In one embodiment, the weighting factors may indicate the relative intensity of stimulation delivered to one selected target tissue site over another selected target tissue site. For example, if processor 70 applies a weighting factor of "6" (on a scale of 1-10) to a first target tissue site and a weighting factor of "4" to a second target tissue site, processor 70 may control IMD 16 to deliver stimulation to the first target tissue site with an intensity of about 60% of a stored intensity value and control IMD 16 to deliver stimulation to the second target tissue site with an intensity at 40% of the stored intensity value. The stored intensity value may be determined by the clinician or may be selected based on the output limitations of IMD 16, which may be the total output limitation of IMD 16 or the output limitations of a particular channel of IMD 16 if IMD 16 is a multichannel device. In addition, in some cases, the stored intensity value may be specific to the particular target tissue site. As described in further detail below, IMD 16 may deliver the therapy to the first and second target tissue sites substantially simultaneously, or in an interleaved or alternating fashion.

In other embodiments, however, the weighting factors do not add up to a particular number (e.g., 1 or 100 percent (%)), but rather, each weighting factor may be independently applied to determine the intensity of stimulation based on a maximum intensity for a given target. The maximum intensities may vary for different targets. In some cases, therapy delivery by IMD 16 may be controlled by determining patient symptoms (or patient mood states) that are observed for patient 14, selecting the one or more target therapy sites for addressing the observed symptoms, and selecting the intensity of stimulation delivered to each target. Each target therapy site may have a weighting factor, which establishes the relative intensity of stimulation for that particular target therapy site based on a scale that is specific to the target therapy site. That is, because target therapy sites may be associated with varying maximum stimulation intensities, the weighting factors may establish the relative intensity of stimulation for a particular target therapy site according to the maximum stimulation intensity associated with the target therapy site.

In another embodiment, the weighting factors may indicate the relative frequency with which therapy is delivered to the respective target tissue sites. For example, if processor 70 applies a weighting factor of "2" to a first target tissue site and a weighting factor of "1" to a second target tissue site, processor 70 may control IMD 16 to deliver stimulation to the first target tissue site at twice the frequency as the second target tissue site. IMD 16 may deliver therapy to the first target tissue site according to a first therapy program and deliver therapy to the second target tissue site according to a second therapy program. The relative higher frequency of stimulation to the first target tissue site may be achieved, for example, by modifying the duty cycles of the first and second therapy programs.

In another embodiment, the weighting factors may generally be used to select therapy programs, regardless of whether the therapy programs are associated with particular stimulation intensities. In addition, the weighting factors may be control therapy based on the patient symptoms, rather than the target tissue sites. For example, processor 70 may establish weighting factors for particular patient symptoms. In some examples, if two or more patient symptoms are associated with the same target tissue site, the weighting factors established for the patient symptoms may be summed, and therapy delivery to the common target tissue site may be controlled based on the summed weighting factors.

After processor 70 determines the target tissue sites and the respective weighting factors, processor 70 may transmit the target tissue sites and respective weighting factors to IMD 16 via the respective telemetry modules 46, 38. Processor 34 of IMD 16 (FIG. 2) may then control therapy delivery to the target tissue sites based on the respective weighting factors. For example, processor 34 of IMD 16 may reference a data structure that associates weighting factors with therapy programs, and control therapy module 32 to deliver therapy to patient 14 in accordance with the therapy programs associated with the weighting factors. In another example, processor 70 of clinician programmer 22 may select the therapy programs that are associated with the weighting factors, based on information stored in memory 72, and transmit the therapy programs to IMD 16 or an indication of the therapy programs to IMD 16.

In some embodiments, the target tissue sites and/or the weights applied to the target tissue sites are dynamic. That is, as the patient's symptoms change, processor 70 may continuously select different target tissue sites and/or update the weighting factors applied to the target tissue sites in accordance with the patient's symptoms. Information relating to the patient's changing symptoms may be received by any suitable technique, such as via input from patient 14, via input from sensing module 26 or any combination thereof. Upon changing the target tissue sites and/or the weighting factors, processor 70 may transmit the weights to IMD 16 via the respective telemetry modules 46, 38. In some cases, electrodes 30, 31 of leads 20 (FIG. 1) may be positioned within brain 12 to deliver stimulation to more than one target tissue site. Accordingly, during the course of chronic therapy delivery, IMD 16 may deliver stimulation to different target tissue sites within brain 12 without the need to change the placement of leads 20 within brain 12 or the configuration of leads 20 (e.g., the type or number of leads implanted within brain 12).

Figure 7:
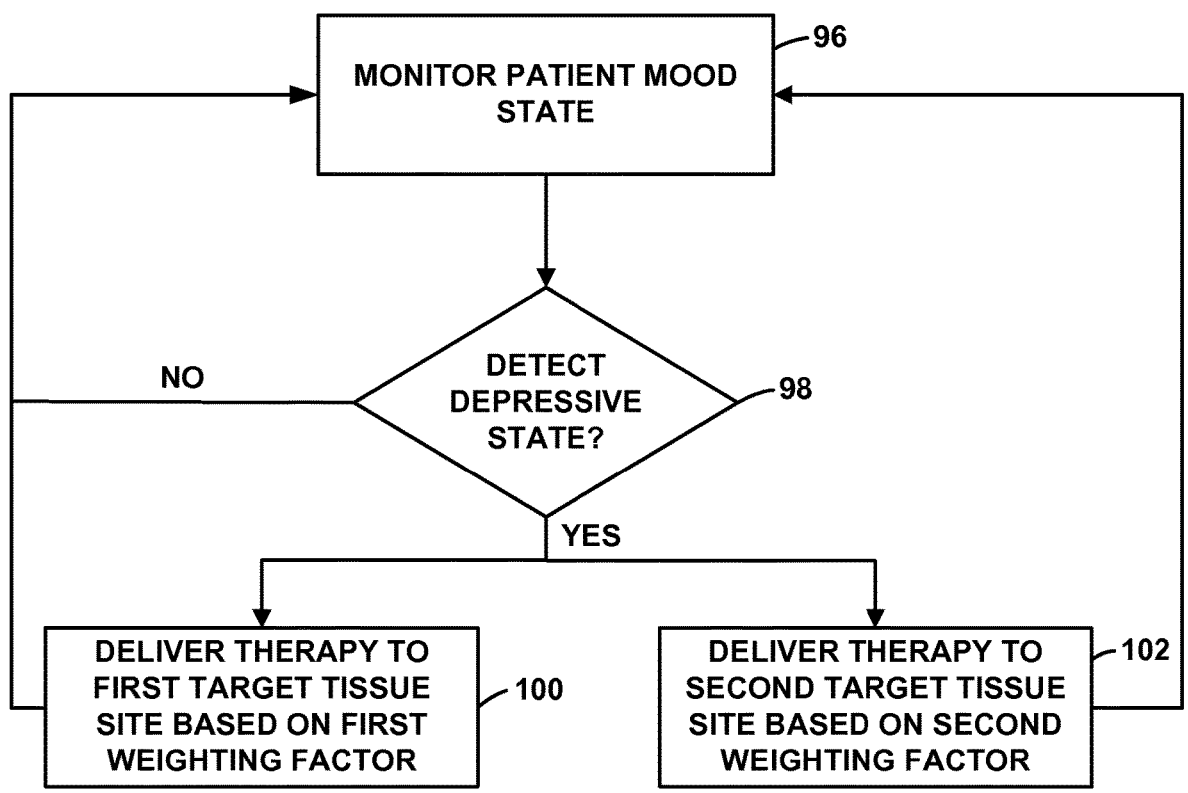
FIG. 7 is a flow diagram illustrating an example technique for controlling therapy delivery to at least two target tissue sites based on a detected mood state.
Figure 8:
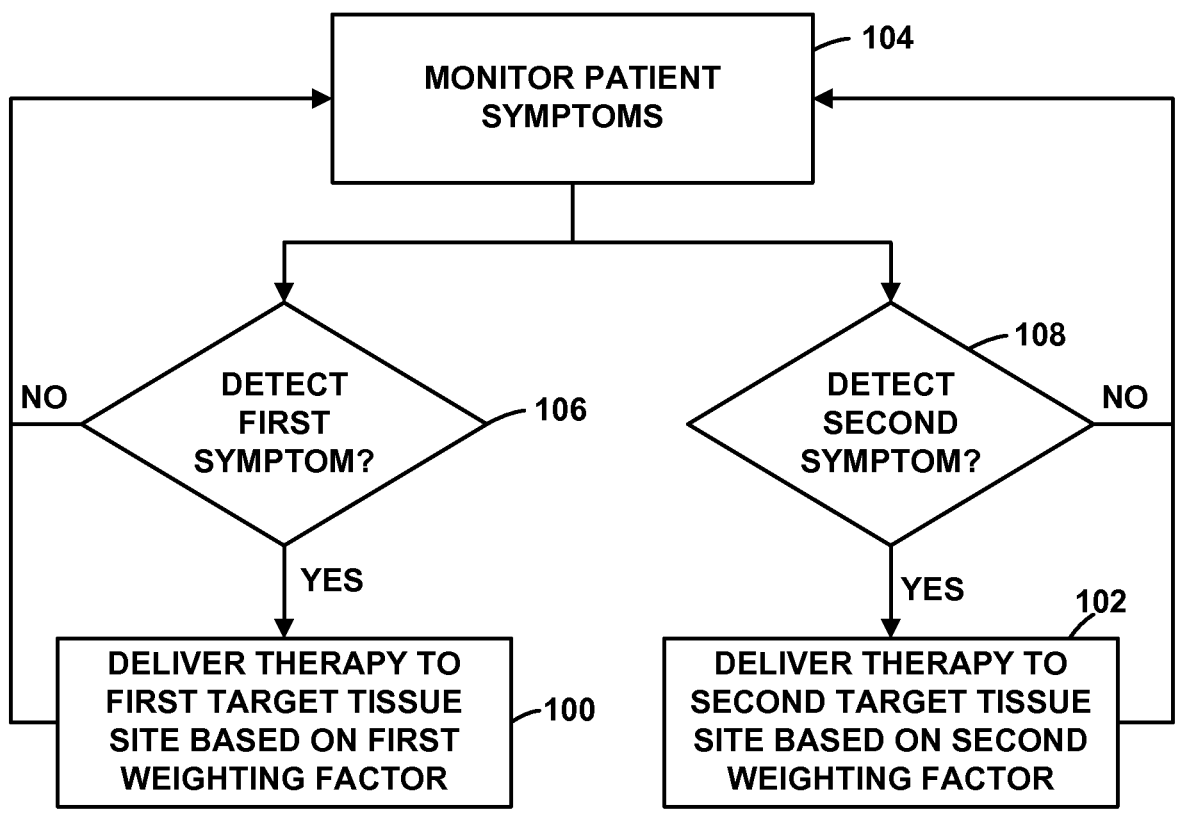
FIG. 8 is a flow diagram illustrating an example technique for controlling therapy delivery to at least two target tissue sites based on detected patient symptoms.
Figure 11:
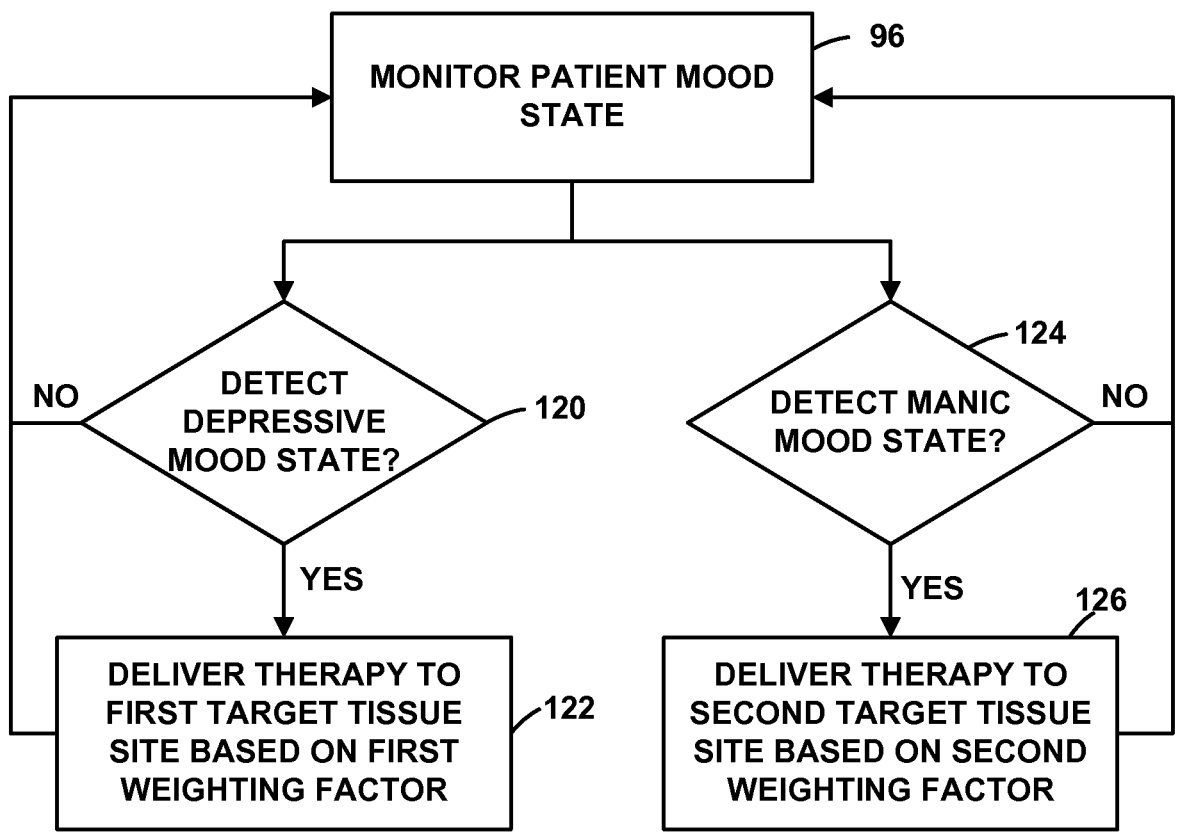
FIG. 11 is a flow diagram of an example technique for controlling therapy delivery to different target tissue sites based on detected mood states.

FIG. 7 is a flow diagram illustrating a technique for delivering therapy to two or more target tissue sites that are selected based on patient symptoms, where the target tissue sites are weighted. While the techniques shown in FIGS. 7, 8, and 11 are primarily described with reference to processor 34 of IMD 16, in other embodiments, processor 70 of clinician programmer 22, processor 70 of patient programmer 24 or a processor of another device may control therapy delivery to two or more target tissue sites according to the technique shown in FIG. 7.

IMD 16 may be configured to provide responsive therapy to patient 14, e.g., by delivering therapy as a particular patient mood state is detected. The mood state may be characterized by the presence of first and second patient symptoms that are each associated with different target therapy sites. In the example technique shown in FIG. 7, processor 34 of IMD 16 may monitor a patient mood state (96) in order to detect a patient mood state that triggers therapy delivery. Processor 34 may, for example, monitor a physiological signal of patient 14, where the signal may be indicative of the patient mood state. Upon detecting a depressive mood state (98), processor 34 may control therapy module 32 to deliver therapy to the first and second targets based on their respective weighting factors (100, 102).

A depressive state may be detected using any suitable technique. In one embodiment, patient 14 provides input indicating the presence of the depressive state, and processor 34 may monitor the patient mood state by, for example, waiting for input from patient 14. The input from patient 14 may be received, e.g., via user interface 44 of patient programmer 24 (FIG. 3). Processor 40 of patient programmer 24 may then transmit the indication of the depressive state to IMD 16 via the respective telemetry modules 46, 38.

In another embodiment, IMD 16 may be include sensing functions or may be coupled to a sensing module 26, and biomarkers indicative of a depressive mood state may be detected. The biomarkers may, for example, detect specific symptoms or physiological effects of the mood state, such as a change in electrical activity of brain 12, changes in concentration of inhibitory or excitatory neurochemicals, changes in proteins, changes in temperature or changes in metabolic rates. The depressive state may be detected by detecting physiological signals other than brain signals, such as a heart rate, respiratory rate, electrodermal activity, facial EMG or thermal activity of the patient's body, as described in U.S. Pat. No. 9,333,350 to Rise et al. and U.S. Provisional Application No. 61/046,210 to Rise et al.

Other techniques for detecting a depressive state or another patient mood state are contemplated. In other embodiments, processor 70 may initiate or otherwise control therapy delivery to patient 14 upon the detection of a mood state other than a depressive state, such as a manic state. The mood state may be characterized by the occurrence of one or more symptoms of the patient's psychiatric disorder. In some examples, the mood state may be, but need not be, characterized by the occurrence of a psychiatric episode, examples of which are discussed above.

IMD 16 may deliver the therapy to the first and second target tissue sites (100, 102) with the same or different leads 20 (FIGS. 1 and 2). Common leads may be used if the first and second target tissue sites are proximate to each other, such that electrodes 30, 31 of leads 20 may be proximate to both the first and second target tissue sites. The therapy may be delivered substantially simultaneously, or in an interleaved or alternating fashion. For example, if IMD 16 delivers stimulation pulses, IMD 16 may deliver pulses to each of the target tissue sites in an alternating or time interleaved fashion, e.g., each pulse delivered to a different target tissue site. IMD 16 may deliver therapy to the different target tissue sites according to different therapy programs, where the programs set forth different pulse rates or duty cycles for the delivery of stimulation, which may result in alternating delivery of therapies. Thus, electrical pulses can be interleaved so as to deliver the same frequency of electrical pulses to respective sites, but with varying amplitudes or pulse widths. Alternatively, a packet of pulses may be delivered to the first target tissue site, with or without ramping of amplitude from start to finish, followed by delivering another packet of pulses to the second target tissue site.

In some embodiments, IMD 16 delivers therapy to the first and second target tissue sites (100, 102) for a predetermined stimulation period, which may be selected by the clinician, or until the depressive state is no longer detected, which may be determined, e.g., based on one or more sensed physiological parameters of patient 16 or based on patient input that is received via patient programmer 24. Accordingly, in some embodiments, after delivering therapy to the first and second target tissue sites (100, 102), IMD 16 continues monitoring the patient mood state (96), as shown in FIG. 7.

In the technique shown in FIG. 7, therapy is delivered to patient 14 to two or more target tissue sites upon detection of a particular mood state (e.g., a depressive state). In other embodiments, therapy may be delivered to the first and second target tissue sites according to their respective weighting factors based on a preset schedule, which may be selected by a user, such as the clinician. The schedule may be stored within memory 35 of IMD 16, memory 42 of clinician programmer 22, and/or memory 72 of patient programmer 24. A schedule may define times for processor 34 of IMD 16 to activate and deactivate therapy delivery to the first and second target tissue sites within patient 14. The schedules may also define times for processor 34 select a particular therapy program or program group, and control therapy delivery module 32 to deliver therapy according to that program or group.

The times for activating and deactivating therapy, as well as the times for selecting particular therapy programs or program groups may be based on, for example, a circadian rhythm of patient 14. For example, some psychiatric disorders are episodic and are worse (i.e., more symptoms are present, or the severity or duration of the symptoms increases) during some times of day (where a day defines a 24 hour period) than other times of day. For example, MDD may be worse in the morning for some patients. Accordingly, the schedule may cause processor 34 to activate therapy delivery during particular time periods in the day and deactivate therapy later, or the schedule may cause processor 34 to select different therapy programs for delivering therapy to the first and second target tissue sites, based on the time of day. The schedule may also set forth the relative frequency with which therapy is delivered to the first and second target tissue sites. A clinician or patient may create, modify, and select schedules using programmers 22 or 24.

In some examples of the technique shown in FIG. 7, IMD 16 delivers therapy to manage the patient's symptoms associated with the patient condition upon detecting a particular mood state, regardless of whether the symptoms are actually detected. However, in some cases, different mood states may be associated with different symptoms. Thus, in some embodiments, processor 34 of IMD 16 may control therapy module 32 to deliver therapy to the first and second target tissue sites based on the detected symptoms associated with the first and second target tissue sites. FIG. 8 is a flow diagram illustrating an example embodiment of a technique for controlling therapy delivery based on detected patient symptoms. After selecting target tissue sites based on patient symptoms, e.g. using the technique described with respect to FIG. 5, processor 34 of IMD 16 may monitor patient symptoms (104). Upon detecting a first patient symptom (106), processor 34 may control therapy module 32 to deliver therapy to the first target tissue site associated with the first patient symptom (100).

Therapy delivery module 32 may deliver therapy to the first target tissue site in accordance with the first weighting factor (100). For example, if the weighting factor affects the frequency with which stimulation signals are delivered to the first target tissue site, therapy delivery module 32 may deliver therapy to the first target tissue site based on the frequency associated with the weighting factor. As another example, processor 34 may select a therapy program associated with the weighting factor and deliver therapy to the first target tissue site according to the selected therapy program.

After delivering therapy to the first target tissue site, e.g., for a predetermined stimulation period or until the stimulation symptom is no longer detected, processor 34 may deactivate therapy delivery to the first target tissue site or at least decrease the intensity of stimulation to the first target tissue site. Processor 34 may then continue monitoring the patient symptoms (104). In this way, closed-loop control of therapy delivery to the first target tissue site may be based on the actual detection of the patient symptom associated with the first target tissue site.

Similarly, upon detecting a second patient symptom (108), processor 34 may control therapy module 32 to deliver therapy to the second target tissue site associated with the second patient symptom (102). In some examples, therapy module 32 may deliver therapy to the second target tissue site at substantially the same time as delivering therapy to the first target tissue site or on an alternating (or interleaved) basis.

Therapy delivery module 32 may deliver therapy to the second target tissue site in accordance with the second weighting factor (102), e.g., by selecting a therapy program associated with the second target tissue site and delivering therapy to the second target tissue site according to the selected therapy program. After delivering therapy to the second target tissue site, e.g., for a predetermined stimulation period or until the stimulation symptom is no longer detected, processor 34 may deactivate therapy delivery to the second target tissue site or at least decrease the intensity of stimulation to the second target tissue site. Processor 34 may then continue monitoring the patient symptoms (104). In this way, closed-loop control of therapy delivery to the second target tissue site may be based on the detection of the patient symptom associated with the second target tissue site.

Processor 34 may monitor patient symptoms using any suitable technique. In some embodiments, the information indicating the occurrence of a patient symptom may include input from patient 14, e.g., provided via patient programmer 24. For example, in one embodiment, programmer 24 may include a dedicated button or another user input mechanism that patient 14 may press or otherwise interact with each time a particular patient symptom occurs, such as each time patient 14 feels a depressed mood, insomnia or hypersomnia. Because a symptom of a depressed mood or another symptom of a psychiatric disorder may not be a discrete event, but, rather, may be a persisting feeling, patient 14 may provide input indicating the occurrence of the symptom at regular intervals, even if the patient symptom was first experienced at an earlier time. In one embodiment, patient programmer 24 may survey patient 14 regarding the existence of various patient symptoms at regular intervals, such as every hour, every few hours or less frequently, such as daily.

Processor 40 of patient programmer 24 (or processor 70 of clinician programmer 22) may receive the input from patient 14 via user interface 44 (FIG. 3) and store an indication, such as a flag, value or signal, upon receipt of the symptom input. Upon reaching a threshold number of symptom indications within a particular time frame (e.g., an hour, days or weeks), processor 40 of patient programmer 24 may determine that the patient symptom is present and therapy delivery is desirable. The threshold number of symptom indications may be determined by the clinician or another user. In some cases, the threshold number of symptom indications may be a single symptom indication or more than one indication. Upon detecting the threshold number of symptom indications, processor 40 may transmit a signal to IMD 16 indicating therapy deliver is desirable. Thus, a certain number of symptom indications may trigger therapy delivery to patient 14 or a modification to a therapy program. Alternatively, processor 34 of IMD 16 may track the number of symptom indications to determine when to control therapy module 32 based on the detection of a symptom.

In another embodiment, processor 34 of IMD 16 may monitor patient symptoms (104) to detect the first and second symptoms (106, 108) by monitoring the patient's activity level. The patient's activity level may be indicative of patient symptoms such as fatigue, loss of energy, insomnia or hypersomnia. Processor 34 may correlate the patient's activity level with a particular time, which may be done with the aid of a clock within IMD 16. For example, if the patient's activity level is relatively high at a time that correlates with the time in which patient 14 is expected to be sleeping, processor 34 may determine that insomnia is present. As another example, if the patient's activity level is relatively low at a time that correlates with the time in which patient 14 is expected to be awake (e.g., during the daylight hours), processor 34 may determine that fatigue, loss of energy or hypersomnia are present. Sensing module 26 (FIG. 1) or a sensing module within IMD 16 may monitor various patient parameters that indicate a patient activity level, such as heart rate, respiration rate, respiratory volume, core temperature, blood pressure, blood oxygen saturation, partial pressure of oxygen within blood, partial pressure of oxygen within cerebrospinal fluid, muscular activity, arterial blood flow, EMG, EEG, ECoG, and ECG.

For example, in some embodiments, processor 34 of IMD 16 may determine activity counts for patient 14, and the activity counts may be used to detect the first or second patient symptoms (106, 108). Examples of determining activity counts are described in U.S. Pat. No. 7,395,113 to Heruth et al., which is entitled, "COLLECTING ACTIVITY INFORMATION TO EVALUATE THERAPY," was filed on Apr. 15, 2004, and issued on Jul. 1, 2008. U.S. Pat. No. 7,395,113 to Heruth et al. is incorporated herein by reference in its entirety.

As described in U.S. Pat. No. 7,395,113 to Heruth et al., processor 34 of IMD 16, processor 70 of clinician programmer 22 or processor 40 of patient programmer 24 may determine a number of activity counts based on signals generated by sensing module 26, and the number of activity counts may be used to determine an activity level of patient 14. For example, the number of activity counts may be a number of threshold crossings by a signal generated by sensing module 26, which may be, for example, an accelerometer or piezoelectric crystal, during a sample period, or a number of switch contacts indicated by the signal generated by sensing module 26, which may be, for example, a mercury switch during a sample period. Upon determining that the activity level (or the number of activity counts) falls above or below a particular threshold level for a certain time range, such as one or more hours or days, processor 34 may determine that the patient symptom is present, and, therefore, it is desirable to deliver therapy to patient 14 to help mitigate the severity or the duration of the patient symptom. In other embodiments, processor 70 of clinician programmer 22 or processor 40 of patient programmer 24 may determine activity counts for patient 14 to detect patient symptoms (106, 108).

Symptoms of the psychiatric disorder that are related to sleep quality, such as insomnia or hypersomnia, may also be detected by monitoring the patient's sleep quality. The quality of the patient's sleep may be determined using any suitable technique. In one embodiment, processor 34 of IMD 16 determines values of one or more sleep metrics that indicate a probability of patient 14 being asleep based on the current value of one or more physiological parameters of patient 14, as described in U.S. Patent Application Pub. No. 2005/0209512 by Heruth et al., which is entitled, "DETECTING SLEEP," was filed on Apr. 15, 2004, and published on Sep. 22, 2005. U.S. Patent Application Pub. No. 2005/0209512 by Heruth et al. is incorporated herein by reference in its entirety. Processor 34 may then determine the number of disruptions in the patient's sleep, e.g., based on the number of times processor 34 determines patient 14 is not asleep during a particular time frame (e.g., about 10 p.m. to about 8 a.m.), which may be selected by the clinician. The time frames referred to in the present disclosure may be specific to patient 14, e.g., based on the behavior or lifestyle of patient 14, or may be general to more than one patient.

As described in U.S. Patent Application Pub. No. 2005/0209512 by Heruth et al., sensing module 26 may generate a signal as a function of at least one physiological parameter of a patient that may discernibly change when the patient is asleep. Example physiological parameters include an activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response of patient 14. In some embodiments, processor 34 determines a value of a sleep metric that indicates a probability of patient 14 being asleep based on a physiological parameter. In particular, processor 34 may apply a function or look-up table to the current value and/or variability of the physiological parameter to determine the sleep metric value. Processor 34 may compare the sleep metric value to a threshold value to determine whether patient 14 is asleep.

In some embodiments, rather than associating target tissue sites with patient symptoms, the target tissue sites may be associated with different patient mood states. Different patient mood states may be associated with different structures within brain 12, and, in some cases, different regions of the same structure. For example, it is believed that therapy delivery to a first target tissue site within brain 12 may provide more effective therapy for a first mood state than a second mood state. Processor 70 may correlate the patient mood states with the structures or regions of a structure of brain 12 in order to select the target tissue sites.

The different patient mood states may be characterized by one or more symptoms, which may differ between patients. For example, in the case of depressive mood state, a patient may exhibit stronger symptoms of fatigue than recurrent thoughts of death. Accordingly, the target tissue sites described above that are associated with fatigue may be associated with depressive mood. As another example, in the case of a manic mood state, the manic mood state may be characterized by a symptom of excessive involvement in pleasurable activities. Accordingly, the target tissue sites described above for anhedonia (the lack of pleasure) may be associated with the manic mood state. However, rather than stimulating to increase pleasure, as in the case of anhedonia, IMD 16 may deliver stimulation to decrease pleasure.

Figures 9, 10:
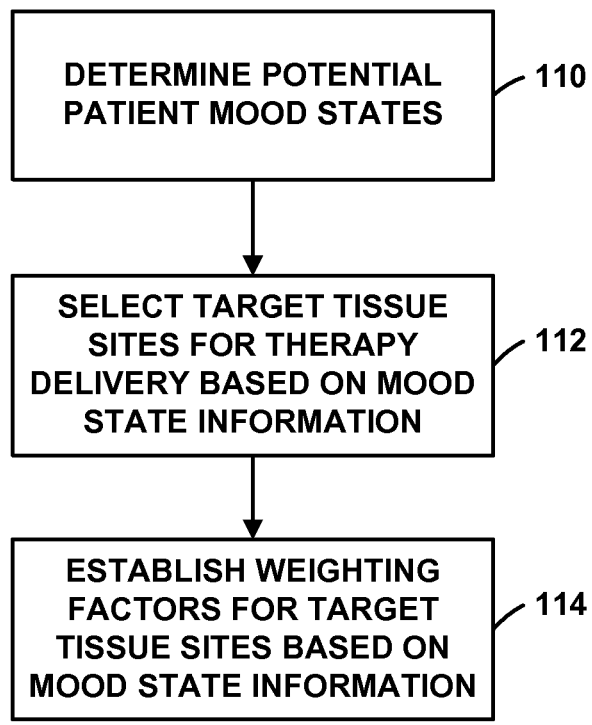
FIG. 9 is a schematic illustration of an example data structure that associates patient mood states with target tissue sites within the brain.
FIG. 10 is a flow diagram illustrating another example technique for selecting the target tissue sites for therapy delivery and establishing weighting factors for the target tissue sites.

The patient mood states may be defined by the clinician and may be selected for a particular patient using patient input and/or any suitable diagnostic tool, such as the surveys described above with reference to FIG. 5. In some embodiments, processor 70 of clinician programmer 22 (FIG. 3) may reference a data structure, such as the one shown in FIG. 9, to select the target tissue sites based on the patient mood state. FIG. 9 illustrates a table that associates patient mood states with target tissue sites within brain 12. The target tissue sites are believed to be sites within brain 12 that are closely related to the respective mood states, such that delivery of electrical stimulation to the target tissue site helps to alleviate or even eliminate the severity or duration of the one or more symptoms associated with the patient mood state.

The target tissue sites may be identified and associated with the patient mood states using any suitable technique. Just as with the technique described above for identifying target tissue sites that are associated with different patient symptoms, the target tissue sites may be identified with the aid of functional medical imaging techniques, such as PET, MRI, fMRI, and MEG. In other embodiments, the target tissue sites may be identified by delivering test therapy (e.g., electrical stimulation or a therapeutic agent) to different target tissue sites within brain 12 and determining which, if any, patient mood states are mitigated (e.g., reduced in severity or decreased in duration) in response to the delivery of therapy. Although FIG. 9 illustrates a table that associates patient mood states with target tissue sites for therapy delivery, in other embodiments, other types of data structures may be stored within memory 42 of clinician programmer 22 or a memory of another device. In FIG. 9, the depressive mood state is associated with the VC/VS, and the manic mood state is associated with the nucleus accumbens. In other examples, each mood state may be associated with more than one target tissue site. In addition, as described above with respect to FIG. 6, memory 72 may store information that associates patient mood state with particular electrode combinations, which may be selected in order to deliver therapy to the tissue site of brain 12 that is associated with the patient mood state.

The different patient mood states may also weighted, and therapy delivery to the different tissue sites associated with the patient mood states may be based on the weighting factors. FIG. 10 is a flow diagram of an example technique for determining weighting factors for the target tissue sites. FIG. 10 is similar to FIG. 5. While processor 70 of clinician programmer 22 is primarily referred to in the description of FIG. 10, in other embodiments, processor 34 of IMD 16 or processor 40 of patient programmer 24 may determine weighting factors according to the example technique shown in FIG. 10 or another suitable technique.

Processor 70 may determine the potential mood states for patient 14 (110). The potential mood states may include any mood states with which patient 14 may possibly experience. The list of potential mood states may be determined, e.g., based on patient input. In other embodiments, the potential mood states may be determined based on the psychiatric condition with which patient 14 is diagnosed. For example, it may be known that patients with bipolar disorder may suffer from depressive, hypomanic, and manic mood states. In some embodiments, processor 70 may store a list of psychiatric disorders and associated potential mood states within memory 72.

Based on the potential mood states, processor 70 may select target tissue sites for therapy delivery (112). The selected target tissue sites may be the tissue sites that are believed to provide efficacious therapy for managing the respective patient mood state. For example, the selected target tissue sites may be associated with patient symptoms that are characteristic of the patient mood state. In one embodiment, processor 70 may reference a data structure similar to that shown in FIG. 9 to determine which target tissue sites are associated with the patient mood state. Accordingly, processor 70 may select the target tissue sites based on information specific to patient 14 or more general information, which may apply to a class of patients afflicted with the specific psychiatric disorder.

Processor 70 may establish weighting factors for the target tissue sites based on the mood state information (114). Just as in the technique shown in FIG. 5 for establishing weighting factors based on patient symptom information, the weighting factors may indicate the relative importance of a selected target tissue site compared to another selected target tissue site. In one embodiment, processor 70 may weigh the target tissue sites based on the relative severity of the mood state associated with the target tissue sites. For example, processor 70 may apply more weight to a first target tissue site compared to a second target tissue site if the first target tissue site is associated with a depressive mood state and the second target tissue site is associated with a manic mood state, and the clinician has determined that the patient's depressive mood states are more severe than the patient's manic mood states.

In another embodiment, processor 70 may weigh the target tissue sites based on the type of mood states associated with the target tissue sites, with little to no regard as to the severity of the mood states. The clinician may provide instructions that, for example, indicate to processor 70 that a first mood state is an absolutely more severe than a second mood state, regardless of the severity rating of the symptoms. The weighting factors for the target tissue sites selected based on patient mood state may be used in a similar manner to the weighting factors for the target tissue sites selected based on patient symptoms (described above).

FIG. 11 is a flow diagram of an example technique for controlling therapy delivery to different target tissue sites within brain 12 of patient 14 based on detected mood states. A patient mood state may be a state in which one or more symptoms of a psychiatric disorder with which the patient is afflicted are observed. Different symptoms or combination of symptoms may be associated with respective mood states. In some embodiments, processor 34 of IMD 16 may control therapy delivery to the different target tissue sites in accordance with weighting factors. The weighting factors may be established using a technique similar to that shown in FIG. 5. In addition, the weighting factors may dynamically change, depending on the patient's mood state and the types and severity of mood states experienced by patient 14, which may change over time or under certain environmental circumstances.

The technique shown in FIG. 11 is similar to the techniques shown in FIG. 7. However, rather than merely detecting a depressive state generally, the technique shown in FIG. 11 detects both a depressive state and a manic state in order to maintain the patient's mood state within a particular range. The technique shown in FIG. 11 may, therefore, be useful for managing a bipolar disorder or MDD of patient 14 or another psychiatric disorder that includes two or more extremes of patient mood states that are undesirable. In other embodiments, different types of patient mood states may be detected, and processor 34 may detect more than two types of mood states.

Processor 34 of IMD 16 may monitor the patient's mood state (96), e.g., using the techniques described above with respect to FIG. 7. If processor 34 detects a first mood state (120), such as by detecting the presence of one or more symptoms that are characteristic of the mood state, processor 34 may control therapy module 32 to deliver electrical stimulation to a first target tissue site (122), which is associated with the first patient mood state. Processor 34 may control therapy module 32 based on the first weighting factor. For example, processor 34 may control therapy module 32 to deliver therapy to the first target tissue site in accordance with a therapy program that has been associated with the first weighting factor. Therapy module 32 may deliver stimulation to the first target tissue site within brain 12 for a predetermined stimulation period, and after the stimulation period, processor 34 may control therapy module 32 to stop therapy delivery to the first target tissue site or to decrease the intensity of stimulation, such as by switching to a therapy program that defines a lower voltage or current amplitude for the stimulation. Thereafter, processor 34 may continue monitoring the patient mood state (96) to determine whether the stimulation therapy was effective.

If the stimulation therapy was not effective, processor 34 may control therapy module 32 to initiate therapy delivery to the first target tissue site (122) for another stimulation period. Alternatively, if therapy module 32 delivers a relatively low intensity stimulation to the first target tissue site, therapy module may modify the therapy delivered to the first target tissue site (122) such that the intensity of the stimulation is greater than the lower intensity stimulation. For example, processor 34 may adjust the amplitude, frequency, signal duration (e.g., pulse width) or other stimulation parameter value of the stimulation therapy. Processor 34 can adjust a stimulation parameter value by selecting another therapy program from memory 32 (FIG. 2) or by adjusting a specific stimulation parameter value of a stored therapy program.

If the stimulation therapy was effective, as determined by the failure to detect the first mood state (120) following the stimulation period, processor 34 may continue monitoring the patient mood state (96) until the first or second mood states are detected. In some embodiments, during the patient mood state monitoring period (96), therapy delivery module 32 may not delivery any stimulation to the first target tissue site. In other embodiments, therapy delivery module 32 may deliver some stimulation to the first target tissue site according to a different therapy program than the therapy program that is used to deliver therapy to the first target tissue site (122) upon detection of the first patient mood state (120).

If processor 34 detects a second mood state, which is different than the first mood state (124), processor 34 may control therapy module 32 to deliver electrical stimulation to a second target tissue site (126), which is associated with the second patient mood state. Processor 34 may monitor for the first and second mood states substantially simultaneously. In addition, processor 34 may deliver therapy to the first and second target tissue sites substantially simultaneously or on an alternating basis.

Again, processor 34 may control therapy delivery module 32 to deliver therapy based on the second weighting factor associated with the second target tissue site. Therapy module 32 may deliver stimulation to the second target tissue site within brain 12 for a predetermined stimulation period, and after the stimulation period, processor 34 may control therapy module 32 to stop therapy delivery to the second target tissue site or to decrease the intensity of stimulation, such as by switching to a therapy program that defines a lower voltage or current amplitude for the stimulation. Thereafter, processor 34 may continue monitoring the patient mood state (96) to determine whether the stimulation therapy delivered to the second target tissue site (126) was effective.

If the stimulation therapy was not effective, processor 34 may control therapy module 32 to initiate therapy delivery to the second target tissue site (126) for another stimulation period. Alternatively, if therapy module 32 delivers a relatively low intensity stimulation to the second target tissue site, therapy module may modify the therapy delivered to the second target tissue site (126) such that the intensity of the stimulation is greater than the lower intensity stimulation. The techniques described for modifying the therapy delivered to the first target tissue site may also be used to modify the therapy delivered to the second target tissue site.

If the delivery of therapy to the second target tissue site was effective, as determined by the failure to detect the second mood state (124) following the stimulation period, processor 34 may continue monitoring the patient mood state (96) until the first or second mood states are detected. In some embodiments, during the patient mood state monitoring period (96), therapy delivery module 32 may not delivery any stimulation to the second target tissue site. In other embodiments, therapy delivery module 32 may deliver some stimulation to the second target tissue site according to a different therapy program than the therapy program that is used to deliver therapy to the second target tissue site (126) upon detection of the second patient mood state (124).

Processor 34 may monitor for the first and second patient mood states in parallel, e.g., substantially simultaneously, or on an interleaved basis. For example, processor 34 may alternate between determining whether the first patient mood state is detected and determining whether the second patient mood state is detected. By detecting more than one mood state and delivering the appropriate therapy to mitigate the detected patient mood state, IMD 16 may help regulate the patient's mood state, such as to maintain the mood state within an acceptable range, e.g., at a mood state between the first and second mood states.

Although therapy system 10 including one IMD 16 is primarily referred to throughout the present disclosure, in other embodiments, a therapy system may include more than one IMD 16. The two or more IMDs of a therapy system may be configured to communicate with each other. In addition, clinician and patient programmers 22, 24 may be configured to communicate with two or more IMDs, such as by sending separate commands to the IMDs or a command that is received by more than one of the IMDs. If a therapy system includes more than one IMD, each IMD may be configured to deliver therapy to a different tissue site of brain 12. This may be useful if the tissue sites are relatively spaced from each other, such that the use of different leads to deliver therapy to the different tissue sites is desirable.

While the description primarily refers to electrical stimulation therapy, in some cases, a therapeutic agent may be delivered to two or more target tissue sites that are selected based upon patient symptoms or patient mood states using the techniques described above. In addition, delivery of the therapeutic agents to the different target tissue sites may be controlled based on a weighting factor associated with the target tissue sites, as described above. The weighting factors may control, for example, the concentration of the therapeutic agent delivered to the target tissue site, the frequency of bolus delivery, the bolus size, as well as the type of therapeutic agent that is delivered.

In addition, in some examples, electrical stimulation therapy can be delivered to a first target and a drug may be delivered to a second target different than the first target, where the first and second targets are selected in accordance with the techniques described herein (e.g., based on patient symptoms and/or mood states).

In the case of therapeutic agent delivery, the therapy parameters may include the dosage of the therapeutic agent (e.g., a bolus size or concentration), the rate of delivery of the therapeutic agent, the maximum acceptable dose in each bolus, a time interval at which a dose of the therapeutic agent may be delivered to a patient (lock-out interval), and so forth. Example therapeutic agents include, but are not limited to, selective serotonin reuptake inhibitor drugs, amitriptyline, amoxapine, benzodiazepines, bupropion, clomipramine, desipramine, doxepin, imipramine, monoamine oxidase inhibitors, maprotiline, mirtazapine, nefazodone, nortriptyline, protriptyline, trazodone, trimipramine, venlafaxines to manage OCD, anxiety disorders or MDD; alprazolam, buspirone, chlordiazepoxide, clonazepam, diazepam, halazepam, lorazepam, oxazepam, prazepam to manage anxiety disorders; and carbamazepine, depakote, divalproex sodium (valproic acid), gabapentin, lamotrigine, lithium carbonate, lithium citrate or topimarate to manage bipolar disorder.

The disclosure also contemplates computer-readable media comprising instructions to cause a processor to perform any of the functions described herein. The computer-readable media may take the form of any volatile, non-volatile, magnetic, optical, or electrical media, such as a RAM, ROM, NVRAM, EEPROM, flash memory, or any other digital media. A programmer, such as clinician programmer 22 or patient programmer 24, may also contain a more portable removable memory type to enable easy data transfer or offline data analysis.

The techniques described in this disclosure, including those attributed to IMD 16, programmers 22, 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments of the disclosure been described. These and other embodiments are within the scope of the following claims.

The invention claimed is:

1. A method of identifying target tissue sites, the method comprising:
   determining, with a processor, a first patient symptom and a second patient symptom of a patient, wherein the first patient symptom differs from the second patient symptom;
   selecting, with the processor, a first target tissue site within the patient for psychiatric disorder therapy delivery based on the first patient symptom;
   selecting, with the processor, a second target tissue site within the patient for the psychiatric disorder therapy delivery based on the second patient symptom, wherein the second target tissue site is different than the first target tissue site;
   establishing, with the processor and based on at least one of a severity, a duration, or a type of the first patient symptom, a first weighting factor for the first target tissue site;
   establishing, with the processor and based on at least one of a severity, a duration, or a type of the second patient symptom, a second weighting factor for the second target tissue site; and
   controlling, by the processor, a medical device to deliver the psychiatric disorder therapy to the first and second target tissue sites substantially simultaneously according to the respective weighting factors,
   wherein, for each of the first and second target tissue sites, the corresponding weighting factor indicates at least one of:
      an intensity of therapy to be delivered to the respective target tissue site when the medical device delivers the psychiatric disorder therapy to the first and second target tissue sites substantially simultaneously,
      a frequency of therapy to be delivered to the respective target tissue site when the medical device delivers the psychiatric disorder therapy to the first and second target tissue sites substantially simultaneously, or
      a therapy program according to which therapy is to be delivered to the respective target tissue site when the medical device delivers the psychiatric disorder therapy to the first and second target tissue sites substantially simultaneously.

2. The method of claim 1, wherein determining the first and second patient symptoms comprises receiving information indicating the first and second patient symptoms.

3. The method of claim 2, wherein receiving information indicating the first patient symptom and the second patient symptom comprises receiving input from the patient identifying at least one of the first or second patient symptoms.

4. The method of claim 2, wherein receiving information comprises receiving information from the patient that rates the severity or the duration of at least one of the first or second patient symptoms.

5. The method of claim 4, wherein receiving information indicating the severity or the duration of the at least one of the first or second patient symptoms comprises receiving input for a plurality of questions, the method further comprising automatically determining the severity or the duration of the at least one of the first or second patient symptoms based on the input for the plurality of questions.

6. The method of claim 2, wherein receiving information indicating the first and second patient symptoms comprises receiving a signal from a sensing module.

7. The method of claim 6, wherein the signal is indicative of at least one of a brain signal, heart rate, respiratory rate, respiratory volume, core temperature, blood pressure, blood oxygen saturation, partial pressure of oxygen within blood, partial pressure of oxygen within cerebrospinal fluid, electrodermal activity, muscle activity, arterial blood flow, or cardiac Q-T interval of the patient.

8. The method of claim 2, wherein receiving information indicating the first patient symptom and the second patient symptom further comprises receiving a signal from a sensing module, wherein the signal is indicative of at least one of the first patient symptom or the second patient symptom.

9. The method of claim 8, wherein the signal is indicative of at least one of a brain signal, heart rate, respiratory rate, respiratory volume, core temperature, blood pressure, blood oxygen saturation, partial pressure of oxygen within blood, partial pressure of oxygen within cerebrospinal fluid, electrodermal activity, muscle activity, arterial blood flow, or cardiac Q-T interval of the patient.

10. The method of claim 1, wherein controlling, by the processor, the medical device to deliver the psychiatric disorder therapy delivery to the first and second target tissue sites substantially simultaneously and according to the respective weighting factors comprises, for each of the first and second target tissue sites:
    selecting the intensity of therapy delivery based on the respective weighting factor; and
    controlling the medical device to deliver the psychiatric disorder therapy to the first and second target tissue sites, substantially simultaneously, based on the selected intensity of therapy delivery.

11. The method of claim 10, wherein the psychiatric disorder therapy comprises electrical stimulation, and the intensity of therapy delivery is a function of at least one of a voltage or current amplitude, signal duration or frequency of electrical stimulation.

12. The method of claim 1, wherein establishing the first and second weighting factors comprises selecting the respective therapy program for the first and second target tissue sites, wherein controlling, by the processor, the medical device to deliver the psychiatric disorder therapy delivery to the first and second target tissue sites comprises controlling the medical device to deliver the psychiatric disorder therapy delivery to the first and second target tissue sites substantially simultaneously according to the selected therapy programs.

13. The method of claim 1, wherein the first patient symptom comprises at least one of fatigue, anhedonia, depressed mood, loss of energy, insomnia or hypersomnia, and the second patient symptom comprises at least one of decreased need for sleep, distractibility, psychomotor agitation, irritable mode or inflated self-esteem.

14. The method of claim 1, wherein selecting the first target tissue site for the psychiatric disorder therapy delivery based on the first patient symptom comprises referencing a data structure that associates a plurality of patient symptoms with respective target tissue sites, the plurality of patient symptoms comprising the first patient symptom, and selecting the first target tissue site associated with the first patient symptom in the data structure.

15. The method of claim 1, wherein selecting the first target tissue site for the psychiatric disorder therapy delivery based on the first patient symptom comprises obtaining a functional medical image of a brain of the patient and selecting the first target tissue site based on the functional medical image, wherein the functional medical image comprises at least one of position emission tomography, magnetic resonance imaging, functional magnetic resonance imaging or magnetoencephalography.

16. The method of claim 1, wherein selecting the first target tissue site based on the first patient symptom comprises:
controlling the medical device to deliver therapy to a trial target tissue site within the patient; and
determining whether the first patient symptom is mitigated in response to the delivery of therapy.

17. The method of claim 1, wherein the first and second symptoms are indicative of a common mood state.

18. The method of claim 1, wherein the first and second symptoms are indicative of different mood states.

19. The method of claim 1, further comprising determining a first mood state of the patient based on the first patient symptom, and determining a second mood state of the patient based on the second patient symptom, wherein the first and second mood states differ, wherein selecting the first target tissue site comprises selecting the first target tissue site associated with the first mood state, and selecting the second target tissue site comprises selecting the second target tissue site associated with the second mood state.

20. The method of claim 1, wherein, for each of the first and second target tissue sites, the corresponding weighting factor indicates the intensity of therapy to be delivered to the respective target tissue site, the intensity being indicated as a percentage of a maximum intensity for a respective target tissue site.

21. The method of claim 20, wherein the maximum intensity for each of the first and second target tissue sites is different.

22. The method of claim 20, wherein the maximum intensity is a combination of a current or voltage amplitude and a signal duration.

23. The method of claim 1, wherein, for one of the first and second target tissue sites, the corresponding weighting factor indicates the intensity of therapy to be delivered to the corresponding target tissue site, the intensity being indicated as a relative intensity of stimulation to be delivered at the one of the first and second target tissue sites.

24. The method of claim 1, wherein the first target tissue site is a first brain structure, the second target tissue site is a second brain structure, and the second brain structure is different than the first brain structure.

25. A method comprising:
selecting a first target tissue site within a patient for psychiatric disorder therapy delivery;
selecting a second target tissue site within the patient for the psychiatric disorder therapy delivery;
establishing, with a processor and based on a severity, a duration, or a type of a first patient symptom, a first weighting factor for the first target tissue site;
establishing, with the processor and based on a severity, a duration, or a type of a second patient symptom, a second weighting factor for the second target tissue site; and
controlling, by the processor, a medical device to deliver the psychiatric disorder therapy delivery to the first and second target tissue sites according to the respective weighting factors,
wherein, for each of the first and second target tissue sites, the corresponding weighting factor indicates at least one of:
an intensity of therapy to be delivered to the respective target tissue site when the medical device delivers the psychiatric disorder therapy to the first and second target tissue sites substantially simultaneously,
a frequency of therapy to be delivered to the respective target tissue site when the medical device delivers the psychiatric disorder therapy to the first and second target tissue sites substantially simultaneously, or
a therapy program according to which therapy is to be delivered to the respective target tissue site when the medical device delivers the psychiatric disorder therapy to the first and second target tissue sites substantially simultaneously.

26. The method of claim 25, further comprising receiving input indicating at least the first patient symptom and the second patient symptom, wherein selecting the first target tissue site comprises selecting the first target tissue based on the first patient symptom and selecting the second target tissue site comprises selecting the second target tissue site based on the second patient symptom.

27. The method of claim 25, further comprising:
determining a first patient mood state, wherein selecting the first target tissue site comprises selecting the first target tissue site based on the first patient mood state; and
determining a second patient mood state, wherein selecting the second target tissue site comprises selecting the second target tissue site based on the second patient mood state.

28. A system comprising:
a memory that stores information associating patient symptoms with target tissue sites for delivery of psychiatric disorder therapy; and
a processor configured to:
determine a first patient symptom and a second patient symptom of a patient, wherein the first patient symptom or mood state differs from the second patient symptom, select a first target tissue site for psychiatric disorder therapy delivery based on the first patient symptom and the information associating patient symptoms with target tissue sites, select a second target tissue site for the psychiatric disorder therapy delivery based on the second patient symptom and the information associating patient symptoms with target tissue sites, wherein the second target tissue site is different than the first target tissue site, establish, based on a severity, a duration, or a type of the first patient symptom, a first weighting factor for the first target tissue site, establish, based on a severity, a duration, or a type of the second patient symptom, a second weighting factor for the second target tissue site, and control a medical device to deliver the psychiatric disorder therapy to the first and second target tissue sites substantially simultaneously according to the respective weighting factors wherein, for each of the first and second target tissue sites, the corresponding weighting factor indicates at least one of:

an intensity of therapy to be delivered to the respective target tissue site when the medical device delivers the psychiatric disorder therapy to the first and second target tissue sites substantially simultaneously, a frequency of therapy to be delivered to the respective target tissue site when the medical device delivers the psychiatric disorder therapy to the first and second target tissue sites substantially simultaneously, or a therapy program according to which therapy is to be delivered to the respective target tissue site when the medical device delivers the psychiatric disorder therapy to the first and second target tissue sites substantially simultaneously.

29. The system of claim 28, wherein the processor is configured to determine the first patient symptom and the second patient symptom by at least receiving information indicating the first patient symptom and the second patient symptom.

30. The system of claim 29, further comprising a user interface, wherein the processor is configured to receive input from a user identifying at least one of the first patient symptom or the second patient symptom, wherein the information indicating the first patient symptom and the second patient symptom comprises the input.

31. The system of claim 30, further comprising a sensing module configured to generate a signal indicative of a patient parameter, wherein the processor is configured to receive the signal and determine at least one of the first patient symptom or the second patient symptom based on the signal and the input from the user.

32. The system of claim 31, wherein the signal is indicative of at least one of a brain signal, heart rate, respiratory rate, respiratory volume, core temperature, blood pressure, blood oxygen saturation, partial pressure of oxygen within blood, partial pressure of oxygen within cerebrospinal fluid, electrodermal activity, muscle activity, arterial blood flow, or cardiac Q-T interval of the patient.

33. The system of claim 29, further comprising a sensing module configured to generate a signal indicative of a patient parameter, wherein the processor is configured to receive the signal and determine at least one of the first patient symptom or the second patient symptom based on the signal.

34. The system of claim 28, wherein the first and second weighting factors indicate the intensity of therapy to be delivered to the respective target tissue site, and wherein the processor is configured to control the medical device to deliver the psychiatric disorder therapy delivery to the first and second target tissue sites, substantially simultaneously, based on the intensity indicated by the respective weighting factor.

35. The system of claim 28, wherein the processor is configured to establish the first and second weighting factors by at least selecting the respective therapy programs for each of the first and second target tissue sites, and wherein the processor is configured to control the medical device to deliver the psychiatric disorder therapy to the first and second target tissue sites, substantially simultaneously, according to the selected therapy programs.

36. The system of claim 28, further comprising a user interface, wherein the processor is configured to receive input from a user identifying the severity or duration of the first patient symptom or the second patient symptom and establish the first or second weighting factor based on the severity or duration of the first patient symptom or the second patient symptom, respectively.

37. The system of claim 28, wherein the first patient symptom comprises at least one of fatigue, anhedonia, depressed mood, loss of energy, insomnia or hypersomnia.

38. The system of claim 28, wherein the first and second symptoms are indicative of a common mood state.

39. The system of claim 28, wherein the first and second symptoms are indicative of different mood states.

40. The system of claim 28, further comprising a user interface, wherein the processor is configured to receive input, via the user interface, indicating a first mood state of the patient, and a second mood state of the patient, the second mood state differing from the first mood state, and wherein the processor is configured to select the first target tissue site by at least selecting the first target tissue site associated with the first mood state in the memory, and select the second target tissue site by at least selecting the second target tissue site associated with the second mood state in the memory.

41. The system of claim 28, wherein, for each of the first and second target tissue sites, the corresponding weighting factor indicates the intensity of therapy to be delivered to the respective target tissue site, the intensity being indicated as a percentage of a maximum intensity for a respective target tissue site.

42. The system of claim 41, wherein the maximum intensity for each of the first and second target tissue sites is different.

43. The system of claim 41, wherein the maximum intensity is a combination of a current or voltage amplitude and a signal duration.

44. The system of claim 28, wherein, for one of the first and second target tissue sites, the corresponding weighting factor indicates the intensity of therapy to be delivered to the corresponding target tissue site, the intensity being indicated as a relative intensity of stimulation to be delivered at the one of the first and second target tissue sites.

* * * * *